US008263056B2

(12) United States Patent
Benson et al.

(10) Patent No.: US 8,263,056 B2
(45) Date of Patent: *Sep. 11, 2012

(54) DYED-HAIR-BINDING PEPTIDES AND PEPTIDE-BASED HAIR REAGENTS FOR PERSONAL CARE

(75) Inventors: R. Edward Benson, Durham, NC (US); Stephen R. Fahnestock, Wilmington, DE (US); Paul Hamilton, Cary, NC (US); John P. O'Brien, Oxford, PA (US); Hong Wang, Kennett Square, PA (US)

(73) Assignees: E I du Pont de Nemours and Company, Wilmington, DE (US); Affinergy Inc

( * ) Notice: Subject to any disclaimer, the term of this patent is extended or adjusted under 35 U.S.C. 154(b) by 987 days.

This patent is subject to a terminal disclaimer.

(21) Appl. No.: 12/198,382

(22) Filed: Aug. 26, 2008

(65) Prior Publication Data

US 2009/0074694 A1    Mar. 19, 2009

Related U.S. Application Data

(60) Provisional application No. 60/972,312, filed on Sep. 14, 2007, provisional application No. 60/972,307, filed on Sep. 14, 2007.

(51) Int. Cl.
*A61K 8/64* (2006.01)
(52) U.S. Cl. .................. 424/70.9; 424/70.1; 424/70.27; 424/70.31; 530/350
(58) Field of Classification Search .................. None
See application file for complete search history.

(56) References Cited

U.S. PATENT DOCUMENTS

| | | | |
|---|---|---|---|
| 5,192,332 A | 3/1993 | Lang et al. | |
| 5,490,980 A | 2/1996 | Richardson et al. | |
| 5,597,386 A | 1/1997 | Igarashi et al. | |
| 6,013,250 A | 1/2000 | Cannell et al. | |
| 6,267,957 B1 | 7/2001 | Green et al. | |
| 6,551,361 B1 | 4/2003 | Cornwell et al. | |
| 6,620,419 B1 | 9/2003 | Lintner | |
| 7,220,405 B2 | 5/2007 | Huang et al. | |
| 2005/0226839 A1 | 10/2005 | Huang et al. | |
| 2005/0229335 A1 | 10/2005 | Huang et al. | |
| 2006/0073111 A1 | 4/2006 | O'Brien et al. | |
| 2006/0222609 A1 | 10/2006 | O'Brien et al. | |
| 2007/0053857 A1 | 3/2007 | Huang et al. | |
| 2007/0065387 A1 | 3/2007 | Beck et al. | |
| 2007/0067924 A1 | 3/2007 | Beck et al. | |
| 2007/0141628 A1 | 6/2007 | Cunningham et al. | |
| 2007/0141629 A1 | 6/2007 | Cunningham et al. | |
| 2007/0196305 A1 | 8/2007 | Wang et al. | |
| 2007/0261775 A1 | 11/2007 | Cunningham et al. | |
| 2007/0264720 A1 | 11/2007 | Cunningham et al. | |
| 2007/0265431 A1 | 11/2007 | Cunningham et al. | |
| 2007/0269394 A1 | 11/2007 | O'Brien et al. | |
| 2008/0107614 A1 | 5/2008 | Fahnestock et al. | |
| 2008/0152612 A1 | 6/2008 | Huang et al. | |
| 2008/0175798 A1 | 7/2008 | Beck et al. | |
| 2008/0207872 A1 | 8/2008 | Cunningham et al. | |
| 2008/0280810 A1 | 11/2008 | O'Brien et al. | |
| 2009/0070944 A1* | 3/2009 | Benson et al. ................ 8/428 |

FOREIGN PATENT DOCUMENTS

| | | |
|---|---|---|
| JP | 08104614 | 4/1996 |
| JP | 09003100 | 1/1997 |
| JP | 2002363026 | 12/2002 |
| WO | 0048558 A1 | 8/2000 |
| WO | 0051556 A1 | 9/2000 |
| WO | 0107009 A1 | 2/2001 |
| WO | 0145652 A1 | 6/2001 |

OTHER PUBLICATIONS

U.S. Appl. No. 11/592,060, filed Nov. 2, 2006, Xueying Huang et al.

* cited by examiner

*Primary Examiner* — Karlheinz R Skowronek
*Assistant Examiner* — Roy Teller
(74) *Attorney, Agent, or Firm* — Roger W. Herrell, Jr.

(57) ABSTRACT

Peptides have been identified that bind with high affinity to dyed hair. Peptide-based hair reagents formed by coupling a dyed-hair-binding peptide to a benefit agent are described. The peptide-based hair reagents include peptide-based hair conditioners and hair colorants. The peptide-based hair conditioners and hair colorants are comprised of a dyed-hair-binding peptide coupled to a hair conditioning agent or a coloring agent, respectively. The peptide-based hair reagents or the dyed-hair-binding peptides may also be used as a protective sealant to improve color retention of dyed hair.

16 Claims, No Drawings

DYED-HAIR-BINDING PEPTIDES AND PEPTIDE-BASED HAIR REAGENTS FOR PERSONAL CARE

This application claims the benefit of U.S. Provisional Patent Application No. 60/972,307, filed Sep. 14, 2007 and U.S. Provisional Patent Application No. 60/972,312, filed Sep. 14, 2007.

FIELD OF THE INVENTION

The invention relates to the field of personal care products. More specifically, the invention relates to dyed-hair-binding peptides and peptide-based hair-binding reagents comprising dyed hair-binding peptides.

BACKGROUND OF THE INVENTION

In hair care and hair coloring compositions, film-forming substances are used to form a protective film on the surface of the hair to protect it from damage due to grooming and styling, shampooing, and exposure to ultraviolet light and the reactive chemicals commonly used in permanent wave agents, hair coloring products, bleaches, and hair straighteners, which denature the hair keratin protein. Moreover, these film-forming substances improve the elasticity of the hair. Film-forming substances that have been used in hair care products include proteins, such as keratin, collagen, soy, and silk proteins and hydrolysates thereof, and polymeric materials, such as polyacrylates, long chain alkyl quaternized amines, and siloxane polymers. For example, Cannell et al. in U.S. Pat. No. 6,013,250 describe a hair care composition for treating hair against chemical and ultraviolet light damage. That composition comprises hydrolyzed protein, having an abundance of anionic amino acids, particularly, sulfur-containing amino acids, and divalent cations. It is proposed in that disclosure that the anionic components of the hydrolyzed protein bind to the hair by means of cationic bridges. Amino acids and their derivatives have also been used in hair care compositions to condition and strengthen hair. For example, O'Toole et al. in WO 00/51556 describe hair care compositions containing four or more amino acid compounds selected from histidine, lysine, methionine, tyrosine, tryptophan, and cysteine compounds.

Hair coloring agents may be divided into three categories, specifically, permanent, semi-permanent or direct, and temporary. The permanent hair dyes are generally oxidative dyes that provide hair color that lasts about four to six weeks. These oxidative hair dyes consist of two parts, one part contains the oxidative dyes in addition to other ingredients, while the second part contains an oxidizing agent such as hydrogen peroxide. The two components are mixed immediately prior to use. The oxidizing agent oxidizes the dye precursors, which then combine to form large color molecules within the hair shaft. Although the oxidative hair dyes provide long-lasting color, the oxidizing agents they contain cause hair damage. The semi-permanent or direct hair dyes are preformed dye molecules that are applied to the hair and provide color for about six to twelve shampoos. This type of hair dye is gentler to the hair because it does not contain peroxides, but the hair color does not last as long. Some improved durability is achieved by the use of nanoparticle hair coloring materials with a particle size of 10 to 500 nm, as described by Hensen et al. in WO 01/045652. These nanoparticle hair coloring materials are conventional direct hair dyes that are treated to obtain nanoscale dimensions and exhibit increased absorption into the hair. Temporary hair dyes are coloring agents that are applied to the hair surface and are removed after one shampoo. It would be desirable to develop a hair coloring agent that provides the durability of the permanent hair dyes without the use of oxidizing agents that damage hair.

The major problem with the current hair care compositions, such as non-oxidative hair dyes, is that they lack the required durability required for long-lasting effects. For this reason, there have been attempts to enhance the binding of the cosmetic agent to the hair, skin or nails. For example, Richardson et al. in U.S. Pat. No. 5,490,980 and Green et al. in U.S. Pat. No. 6,267,957 describe the covalent attachment of cosmetic agents, such as skin conditioners, hair conditioners, coloring agents, sunscreens, and perfumes, to hair, skin, and nails using the enzyme transglutaminase. This enzyme cross-links an amine moiety on the cosmetic agent to the glutamine residues in skin, hair, and nails. Similarly, Green et al. in WO 01/07009 describe the use of the enzyme lysine oxidase to covalently attach cosmetic agents to hair, skin, and nails.

In another approach, cosmetic agents have been covalently attached to proteins or protein hydrolysates. For example, Lang et al. in U.S. Pat. No. 5,192,332 describe temporary coloring compositions that contain an animal or vegetable protein, or hydrolysate thereof, which contain residues of dye molecules grafted onto the protein chain. In those compositions, the protein serves as a conditioning agent and does not enhance the binding of the cosmetic agent to hair. Horikoshi et al. in JP 08104614 and Igarashi et al. in U.S. Pat. No. 5,597,386 describe hair coloring agents that consist of an anti-keratin antibody covalently attached to a dye or pigment. The antibody binds to the hair, thereby enhancing the binding of the hair coloring agent to the hair. Similarly, Kizawa et al. in JP 09003100 describe an antibody that recognizes the surface layer of hair and its use to treat hair. A hair coloring agent consisting of that anti-hair antibody coupled to colored latex particles is also described. The use of antibodies to enhance the binding of dyes to the hair is effective in increasing the durability of the hair coloring, but these antibodies are difficult and expensive to produce. Terada et al. in JP 2002363026 describe the use of conjugates consisting of single-chain antibodies, preferably anti-keratin, coupled to dyes, ligands, and cosmetic agents for skin and hair care compositions. The single-chain antibodies may be prepared using genetic engineering techniques, but are still difficult and expensive to prepare because of their large size. Findlay in WO 00/048558 describes the use of calycin proteins, such as β-lactoglobulin, which contain a binding domain for a cosmetic agent and another binding domain that binds to at least a part of the surface of a hair fiber or skin surface, for conditioners, dyes, and perfumes. Again these proteins are large and difficult and expensive to produce.

Linter in U.S. Pat. No. 6,620,419 describes peptides grafted to a fatty acid chain and their use in cosmetic and dermopharmaceutical applications. The peptides described in that disclosure are chosen because they stimulate the synthesis of collagen; they are not specific binding peptides that enhance the durability of hair and skin conditioners, and hair, nail, and skin colorants.

Hair binding peptides and their use in peptide-based reagents for the targeted delivery of benefit agents (i.e. "hair treatment reagents") have been described in commonly owned U.S. Pat. No. 7,220,405 and U.S. patent application Ser. Nos. 11/074,473; 11/592,060; 11/592,108; 11/716,161; 11/093,873; 11/607,732; 11/359,163; 11/512,910; 11/514,804; 11/251,715; 11/389,948; 11/778,699; 11/607,792; 11/11/607,723; 11/607,734; 11/607,672; 11/607,673; 11/923,829; 11/877,692; and 11/939,583. Even though various hair binding peptides have been previously reported, there remains a need to identify additional hair binding peptides, especially hair-binding peptides exhibiting strong affinity for dyed hair.

Co-pending U.S. patent application Ser. No. 11/512,910 (corresponding to U.S. patent application publication no. 2007/0067924) describes a method for enhancing the effects of traditional and non-traditional colorants, conditioners, and other benefit agents with the application of a peptide-based sealant. Peptides having an affinity for non-dyed hair are provided including shampoo and/or conditioner resistant hair-binding peptides. Peptides selected for having an affinity to dyed hair are not described.

Cornwell et al. (U.S. Pat. No. 6,551,361) describe a method for reducing color loss from hair treated with an oxidative hair dye comprising contacting the hair, either before or after treatment of the hair with the oxidative hair dye, with an organic amino compound, such as basic amino acids, urea, guanidine, and salts or mixtures thereof. However, that disclosure does not describe the use of specific hair-binding peptides, or conjugates comprising dyed-hair-binding peptides coupled to a benefit agent as sealants for colorants and conditioners.

The problem to be solved is to provide peptides that have a strong affinity for dyed hair. Dyed-hair-binding peptide can be used to deliver benefits agents to the surface of dyed hair or may be used as a peptide-based sealant to improve or enhance traditional colorants and conditioners.

Applicants have met the stated needs by identifying dyed-hair-binding peptides exhibiting strong affinity for dyed hair. The dyed hair-binding peptides can be used to prepare peptide-based reagents for the targeted delivery of benefit agents to dyed hair or may be used as a peptide-based sealant to improve the color durability of dyed hair.

SUMMARY OF THE INVENTION

The invention provides peptides that bind with high affinity to dyed hair. The invention also provides peptide-based conditioners and colorants for dyed hair. In one embodiment, the peptide-based conditioners and colorants are diblock or triblock compositions.

Accordingly, the invention provides dyed-hair-binding peptides having a sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 30, 31, 32, 33, and 34.

In another embodiment the invention provides a peptide-based hair reagent having the general structure $(DHBP)_n$—BA or $[(DHBP)_m$—$S]_n$—BA;

wherein
a) DHBP is a hair-binding peptide;
b) BA is a benefit agent; and
c) n ranges from 1 to about 1,000;
d) m ranges from 1 to about 50; and
e) S is a spacer;
wherein the dyed-hair-binding peptide has a sequence selected from the group consisting of SEQ ID NOs 1, 2, 3, 4, 5, 6, 7, 8, 9, 10, 11, 12, 13, 14, 15, 16, 17, 18, 19, 20, 21, 22, 23, 24, 25, 26, 27, 30, 31, 32, 33, and 34.

In a further embodiment, the benefit agent is selected from the group consisting of conditioning agents, coloring agents, and sunscreen agents.

In another embodiment, a hair care composition comprising an effective amount of the peptide-based hair reagent or an effective amount of at least one of the present dyed-hair-binding peptides is also provided.

In another embodiment, a method for applying a benefit agent to dyed hair is also provided comprising contacting dyed hair with the peptide-based hair reagent whereby the dyed-hair-binding peptide adheres to dyed hair.

In another embodiment, a method to form a protective layer on the surface of dyed hair is provided comprising contacting dyed hair under suitable conditions with an effective amount of a peptide-based hair reagent or an effective amount of a dyed-hair-binding peptide of the present invention whereby the dyed-hair-binding peptide adheres to said dyed hair.

In a preferred embodiment, the protective layer adhered to dyed hair improves color durability or color retention.

BRIEF DESCRIPTION OF SEQUENCE DESCRIPTIONS

The invention can be more fully understood from the following detailed description and the accompanying sequence descriptions, which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence of dyed hair-binding peptide Dye-1.
SEQ ID NO: 2 is the amino acid sequence of dyed hair-binding peptide Dye-2.
SEQ ID NO: 3 is the amino acid sequence of dyed hair-binding peptide Dye-3.
SEQ ID NO: 4 is the amino acid sequence of dyed hair-binding peptide Dye-4.
SEQ ID NO: 5 is the amino acid sequence of dyed hair-binding peptide Dye-5.
SEQ ID NO: 6 is the amino acid sequence of dyed hair-binding peptide Dye-6.
SEQ ID NO: 7 is the amino acid sequence of dyed hair-binding peptide Dye-7.
SEQ ID NO: 8 is the amino acid sequence of dyed hair-binding peptide Dye-8.
SEQ ID NO: 9 is the amino acid sequence of dyed hair-binding peptide Dye-9.
SEQ ID NO: 10 is the amino acid sequence of dyed hair-binding peptide Dye-10.
SEQ ID NO: 11 is the amino acid sequence of dyed hair-binding peptide Dye-11.
SEQ ID NO: 12 is the amino acid sequence of dyed hair-binding peptide Dye-12.
SEQ ID NO: 13 is the amino acid sequence of dyed hair-binding peptide Dye-13.
SEQ ID NO: 14 is the amino acid sequence of dyed hair-binding peptide Dye-14.
SEQ ID NO: 15 is the amino acid sequence of dyed hair-binding peptide Dye-15.
SEQ ID NO: 16 is the amino acid sequence of dyed hair-binding peptide Dye-16.
SEQ ID NO: 17 is the amino acid sequence of dyed hair-binding peptide Dye-17.

SEQ ID NO: 18 is the amino acid sequence of dyed hair-binding peptide Dye-18.

SEQ ID NO: 19 is the amino acid sequence of dyed hair-binding peptide Dye-19.

SEQ ID NO: 20 is the amino acid sequence of dyed hair-binding peptide Dye-20.

SEQ ID NO: 21 is the amino acid sequence of dyed hair-binding peptide Dye-21.

SEQ ID NO: 22 is the amino acid sequence of dyed hair-binding peptide Dye-22.

SEQ ID NO: 23 is the amino acid sequence of dyed hair-binding peptide Dye-23.

SEQ ID NO: 24 is the amino acid sequence of dyed hair-binding peptide Dye-24.

SEQ ID NO: 25 is the amino acid sequence of dyed hair-binding peptide Dye-25.

SEQ ID NO: 26 is the amino acid sequence of dyed hair-binding peptide Dye-26.

SEQ ID NO: 27 is the amino acid sequence of dyed hair-binding peptide Dye-27.

SEQ ID NO: 28 is the amino acid sequence of dyed hair-binding peptide Dye-28.

SEQ ID NO: 29 is the amino acid sequence of dyed hair-binding peptide AFF-15011.

SEQ ID NO: 30 is the amino acid sequence of dyed hair-binding peptide AFF-15013.

SEQ ID NO: 31 is the amino acid sequence of dyed hair-binding peptide AFF-15016.

SEQ ID NO: 32 is the amino acid sequence of dyed hair-binding peptide AFF-15027.

SEQ ID NO: 33 is the amino acid sequence of dyed hair-binding peptide AFF-15029.

SEQ ID NO: 34 is the amino acid sequence of dyed hair-binding peptide AFF-15030.

SEQ ID NO: 35 is the amino acid sequence of dyed hair-binding peptide AFF-15025 without the linker used to attach biotin.

SEQ ID NO: 36 is the amino acid sequence of dyed hair-binding peptide AFF-15025 with the linker used to attach biotin.

SEQ ID NO: 37 is the amino acid sequence of the linker GSSGK used to attach biotin.

SEQ ID NO: 38 is the amino acid sequence of the Caspase-3 cleavage sequence.

DETAILED DESCRIPTION OF THE INVENTION

The present invention provides dyed-hair-binding peptide sequences that specifically bind to human dyed-hair with high affinity. Additionally, the present invention provides peptide-based dyed-hair-treatment reagents comprising the present dyed-hair-binding peptides coupled with various benefit agents that convey a benefit to the dyed hair surface. Typical of the compositions of the invention are peptide-based hair conditioners and hair colorants with improved durability.

A method to form a protective layer on the surface of dyed hair to improve color retention and durability is also provided. The protective layer can be formed by the present dyed-hair-binding peptides or by using peptide-based hair reagents comprising at least one of the present dyed-hair-binding peptides.

The following definitions are used herein and should be referred to for interpretation of the claims and the specification.

"DHBP" means dyed-hair-binding peptide. A "dyed-hair-binding peptide" is a peptide having strong affinity for dyed hair. In another embodiment, the DHBP has a stronger affinity (as measured by a lower $K_d$ or $MB_{50}$ value) for dyed hair over normal, non-dyed hair. In one embodiment, the dyed-hair-binding peptide is selected from a combinatorially generated library. In another embodiment, the combinatorially generated dyed-hair-binding peptide is selected using a biopanning process selected from the group consisting of phage display, yeast display, bacterial display, ribosome display, and mRNA-display.

"HCA" means hair conditioning agent. The hair conditioning agent is an agent used to condition normal, bleached, or dyed hair. In a preferred embodiment, the HCA is an agent suitable for conditioning dyed hair.

"C" means coloring agent for hair.

"S" means spacer.

"BA" means benefit agent.

The term "peptide" refers to two or more amino acids joined to each other by peptide bonds or modified peptide bonds.

The term "dyed hair surface" will mean the surface of the human dyed hair that may serve as a substrate for the binding of a dyed-hair-binding peptide or a peptide-based hair reagent comprising a dyed-hair-binding peptide.

The term "dyed hair" is used herein to refer to hair that has been treated with a hair dye. In one embodiment, the dye is permanent or semi-permanent. In another embodiment, the dye is a cationic, semi-permanent dye. In another embodiment, the dye is Basic Brown 17.

The term "hair" as used herein refers to human hair, eyebrows, and eyelashes.

The term "benefit agent" is a general term applying to a compound or substance that may be coupled with a binding peptide for application to a dyed hair. Benefit agents typically include conditioners (including sealants), colorants, fragrances, sunscreen agents, and the like along with other substances commonly used in the personal care industry. In one embodiment, the dyed-hair-binding peptide is the benefit agent (for example, a peptide-based conditioning agent). In another embodiment, the benefit agent is a silk-like peptide as described in U.S. Pat. No. 7,060,260 and U.S. patent application Ser. No. 11/923,829.

The term "linking domain" or "linker domain" as used herein applies to a particular type of active domain that is used to either link two domains together, as a separator ("spacer") between two domains, or a domain and a terminal end. Linking domains may have a function beyond joining or separating two domains of a peptide.

The terms "coupling" and "coupled" as used herein refer to any chemical association and includes both covalent and non-covalent interactions. In one embodiment, the coupling is non-covalent. In another embodiment, the coupling is covalent.

The term "stringency" as it is applied to the selection of the dyed-hair-binding peptides of the present invention, refers to the concentration of the eluting agent (usually detergent) used to elute peptides from the hair surface. Higher concentrations of the eluting agent provide more stringent conditions.

The term "peptide-hair complex" or "peptide-substrate complex" means a structure comprising a peptide bound to a dyed hair fiber via a binding site on the peptide.

The term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with its corresponding substrate.

The term "binding affinity" refers to the strength of the interaction of a binding peptide with its respective substrate. The binding affinity can be defined or measured in terms of $K_d$, $EC_{50}$, or $MB_{50}$. In one embodiment, the binding affinity is determined in terms of the $MB_{50}$ value using an ELISA-based binding assay (see Example 4)

The term "nanoparticles" are herein defined as particles with an average particle diameter of between 1 and 100 nm. Preferably, the average particle diameter of the particles is between about 1 and 40 nm. As used herein, "particle size" and "particle diameter" have the same meaning. Nanoparticles include, but are not limited to, metallic, semiconductor, polymer, or silica particles.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

The term "phage" or "bacteriophage" refers to a virus that infects bacteria. Altered forms may be used for the purpose of the present invention. The preferred bacteriophage is derived from the "wild" phage, called M13. The M13 system can grow inside a bacterium, so that it does not destroy the cell it infects but causes it to make new phages continuously. It is a single-stranded DNA phage.

The term "phage display" refers to the display of functional foreign peptides or small proteins on the surface of bacteriophage or phagemid particles. Genetically engineered phage may be used to present peptides as segments of their native surface proteins. Peptide libraries may be produced by populations of phage with different gene sequences.

"PCR" or "polymerase chain reaction" is a technique used for the amplification of specific DNA segments (U.S. Pat. Nos. 4,683,195 and 4,800,159).

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

The present invention comprises specific dyed-hair-binding peptides and their use in peptide-based hair reagents as conditioners and coloring agents for hair.

Dyed-Hair-Binding Peptides

Dyed hair-binding peptides as defined herein are peptide sequences that bind with high affinity to dyed hair. Human hair samples are available commercially, for example from International Hair Importers and Products (Bellerose, N.Y.), in different colors, such as brown, black, red, and blond, and in various types, such as African-American, Caucasian, and Asian. Additionally, the hair samples may be treated for example using hydrogen peroxide to obtain bleached hair.

Dyed hair-binding peptides of the present invention are selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 29, 29, 30, 31, 32, 33 and 34. The dyed hair-binding, peptides of the present invention are typically from about 7 amino acids to about 27 amino acids, more preferably, from about 7 amino acids to about 20 amino acids, most preferably from about 7 to about 12 amino acids.

In one embodiment, the dyed hair-binding peptides of the present invention are characterized by their high affinity for dyed hair. In one embodiment, the dyed hair-binding peptides have a binding affinity, as measured by $MB_{50}$ values, of less than or equal to about $10^{-2}$ M, less than or equal to about $10^{-3}$ M, less than or equal to about $10^{-4}$ M, less than or equal to about $10^{-5}$ M, preferably less than or equal to about $10^{-6}$ M, and more preferably less than or equal to about $10^{-7}$ M.

Suitable dyed hair-binding, peptide sequences may be selected using methods that are well known in the art. The peptides of the present invention are generated randomly and then selected against a specific hair sample based upon their binding affinity for the substrate of interest. The generation of random libraries of peptides is well known and may be accomplished by a variety of techniques including, bacterial display (Kemp, D. J.; *Proc. Natl. Acad. Sci. USA* 78(7):4520-4524 (1981), and Helfman et al., *Proc. Natl. Acad. Sci. USA* 80(1):31-35, (1983)), yeast display (Chien et al., *Proc Natl Acad Sci USA* 88(21):9578-82 (1991)), combinatorial solid phase peptide synthesis (U.S. Pat. Nos. 5,449,754, 5,480,971, 5,585,275, 5,639,603), and phage display technology (U.S. Pat. Nos. 5,223,409, 5,403,484, 5,571,698, 5,837,500); ribosome display (U.S. Pat. Nos. 5,643,768; 5,658,754; and 7,074,557), and mRNA display technology (PROFUSION™; U.S. Pat. Nos. 6,258,558; 6,518,018; 6,281,344; 6,214,553; 6,261,804; 6,207,446; 6,846,655; 6,312,927; 6,602,685; 6,416,950; 6,429,300; 7,078,197; and 6,436,665). Techniques to generate such biological peptide libraries are described in Dani, M., *J. of Receptor & Signal Transduction Res.*, 21 (4):447-468 (2001).

A preferred method to randomly generate peptides is by phage display. Since its introduction in 1985, phage display has been widely used to discover a variety of ligands including peptides, proteins and small molecules for drug targets (Dixit, *J. of Sci. & Ind. Research*, 57:173-183 (1998)). The applications have expanded to other areas such as studying protein folding, novel catalytic activities, DNA-binding proteins with novel specificities, and novel peptide-based biomaterial scaffolds for tissue engineering (Hoess, *Chem. Rev.* 101:3205-3218 (2001) and Holmes, *Trends Biotechnol.* 20:16-21 (2002)). Whaley et al. (Nature 405:665-668 (2000)) disclose the use of phage display screening to identify peptide sequences that can bind specifically to different crystallographic forms of inorganic semiconductor substrates.

A modified screening method that comprises contacting a peptide library with an anti-target to remove peptides that bind to the anti-target, then contacting the non-binding peptides with the target has been described (Estell et al. WO 01/079479, Murray et al. U.S. Patent Application Publication No. 2002/0098524, and Janssen et al. U.S. Patent Application Publication No. 2003/0152976). Using that method, a peptide sequence that binds to hair and not to skin and a peptide sequence that binds to skin and not hair were identified. Using the same method, Janssen et al. (WO 04/048399) identified other skin-binding and hair-binding peptides, as well as several other binding motifs.

Phage display is a selection technique in which a peptide or protein is genetically fused to a coat protein of a bacteriophage, resulting in display of fused peptide on the exterior of the phage virion, while the DNA encoding the fusion resides within the virion. This physical linkage between the displayed peptide and the DNA encoding it allows screening of vast numbers of variants of peptides, each linked to a corresponding DNA sequence, by a simple in vitro selection procedure called "biopanning". As used herein, "biopanning" may be used to describe any selection procedure (phage display, ribosome display, mRNA-display, etc.) where a library of displayed peptides a library of displayed peptides is panned against a specified target material (e.g. hair). In its simplest form, phage display biopanning is carried out by incubating the pool of phage-displayed variants with a target of interest that has been immobilized on a plate or bead, washing away unbound phage, and eluting specifically bound phage by disrupting the binding interactions between the phage and the target. The eluted phage is then amplified in vivo and the process is repeated, resulting in a stepwise enrichment of the phage pool in favor of the tightest binding sequences. After 3 or more rounds of selection/amplification, individual clones are characterized by DNA sequencing.

Specifically, the dyed hair-binding domains may be selected using the following method. A suitable library of phage-peptides is generated using the methods described above or the library is purchased from a commercial supplier. After the library of phage-peptides has been generated, they are then contacted with an appropriate amount of the substrate. The library of phage-peptides is dissolved in a suitable solution for contacting the substrate. The test substrate may be suspended in the solution or may be immobilized on a plate or bead. A preferred solution is a buffered aqueous saline solution containing a surfactant. A suitable solution is Tris-buffered saline (TBS) with 0.05 to 0.5% TWEEN® 20. The solution may additionally be agitated by any means in order to increase the mass transfer rate of the peptides to the substrate, thereby shortening the time required to attain maximum binding.

Upon contact, a number of the randomly generated phage-peptides will bind to the substrate to form a phage-peptide-substrate complex. Unbound phage-peptide may be removed by washing. After all unbound material is removed, phage-peptides having varying degrees of binding affinities for the substrate may be fractionated by selected washings in buffers having varying stringencies. Increasing the stringency of the buffer used increases the required strength of the bond between the phage-peptide and substrate in the phage-peptide-substrate complex.

A number of substances may be used to vary the stringency of the buffer solution in peptide selection including, but not limited to, acidic pH (1.5-3.0); basic pH (10-12.5); high salt concentrations such as $MgCl_2$ (3-5 M) and LiCl (5-10 M); water; ethylene glycol (25-50%); dioxane (5-20%); thiocyanate (1-5 M); guanidine (2-5 M); urea (2-8 M); and various concentrations of different surfactants such as SDS (sodium dodecyl sulfate), DOC (sodium deoxycholate), Nonidet P-40, Triton X-100, TWEEN® 20, wherein TWEEN® 20 is preferred. These substances may be prepared in buffer solutions including, but not limited to, Tris-HCl, Tris-buffered saline, Tris-borate, Tris-acetic acid, triethylamine, phosphate buffer, and glycine-HCl, wherein Tris-buffered saline solution is preferred.

It will be appreciated that phage-peptides having increasing binding affinities for the substrate may be eluted by repeating the selection process using buffers with increasing stringencies. The eluted phage-peptides can be identified and sequenced by any means known in the art.

In one embodiment, the following method for generating the dyed hair-binding peptides may be used. A library of combinatorially generated phage-peptides is contacted with a substrate (e.g., regular hair; i.e. hair that has not been dyed or bleached) to form phage peptide-substrate complexes. The phage-peptide-substrate complex is separated from uncomplexed peptides and unbound substrate, and the bound phage-peptides from the phage-peptide-substrate complexes are eluted from the complex, preferably by acid treatment. Then, the eluted phage-peptides are identified and sequenced. To identify peptide sequences that bind to the target substrate but not to other substrates, a subtractive panning step may be added. Specifically, the library of combinatorially generated phage-peptides is first contacted with the non-target to remove phage-peptides that bind to it. Then, the non-binding phage-peptides are contacted with target substrate and the above process is followed. Alternatively, the library of combinatorially generated phage-peptides may be contacted with the non-target and the target simultaneously. Then, the phage-peptide-substrate complexes are separated from the phage-peptide-non-target complexes and the method described above is followed for the desired phage-substrate complexes.

Alternatively, a modified phage display screening method for isolating peptides with a higher affinity for hair may be used. In the modified method, the phage-peptide-substrate complexes are formed as described above. Then, these complexes are treated with an elution buffer. Any of the elution buffers described above may be used. Preferably, the elution buffer is an acidic solution. Then, the remaining, elution-resistant phage-peptide-substrate complexes are used to directly infect/transfect a bacterial host cell, such as E. coli ER2738. The infected host cells are grown in an appropriate growth medium, such as LB (Luria-Bertani) medium, and this culture is spread onto agar, containing a suitable growth medium, such as LB medium with IPTG (isopropyl β-D-thiogalactopyranoside) and S-Gal™. After growth, the plaques are picked for DNA isolation and sequencing to identify the peptide sequences with a high binding affinity for the substrate of interest. Alternatively, PCR may be used to identify the elution-resistant phage-peptides from the modified phage display screening method, described above, by directly carrying out PCR on the phage-peptide-substrate complexes using the appropriate primers, as described by Janssen et al. in U.S. Patent Application Publication No. 2003/0152976.

The present dyed hair-binding peptides can be used in peptide-based hair treatment reagents having multiple functional units or "blocks" wherein each block provides a defined function to the overall reagent. In one embodiment, the peptide-based hair reagent is a diblock or triblock structure having the general structure:

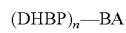

or

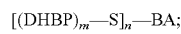

wherein
a) DHBP is at least one of the present dyed-hair-binding peptides;
b) BA is a benefit agent;
c) n ranges from 1 to about 1,000;
d) m ranges from 1 to about 50; and
e) S is a spacer.

In one embodiment, the benefit agent is selected from the group consisting of colorants, conditioners, and sunscreen agents. In another embodiment, the benefit agent is selected from the group consisting of colorants and conditioners. In another embodiment, the dyed-hair-binding peptide acts as a benefit agent (e.g. a peptide conditioner or sealant). In another embodiment, the present dyed-hair-binding peptides or peptide-based hair reagent (comprising at least one of the present dyed-hair-binding peptides) are used in hair care compositions as a sealant on dyed hair to retain color or appearance.

Binding Affinity

The present hair-binding peptides exhibit a strong affinity for dyed hair. The affinity of the peptide for the dyed hair can be expressed in terms of the dissociation constant $K_d$. $K_d$ (expressed as molar concentration) corresponds to the concentration of peptide at which the binding site on the target is half occupied, i.e., when the concentration of target with peptide bound (bound target material) equals the concentration of target with no peptide bound. The smaller the dissociation constant, the more tightly bound the peptide is; for example, a peptide with a nanomolar (nM) dissociation constant binds more tightly than a peptide with a micromolar (μM) dissociation constant. In one embodiment, the present dyed hair-binding peptides have a $K_d$ of $10^{-3}$ M or less, preferably $10^{-4}$ M or less, more preferably $10^{-5}$ M or less, even more preferably $10^{-6}$ M or less, yet even more preferably $10^{-7}$ M or less, and most preferably $10^{-8}$ M or less.

Alternatively, one of skill in the art can also use an ELISA-based assay to calculate a relative affinity of the peptide for the target material (reported as an $MB_{50}$ value; see present Example 3 and co-owned U.S. Patent Application Publication 2005/022683). As used herein, the term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with its corresponding substrate. In one embodiment, the $MB_{50}$ value (reported in terms of molar concentration) for the dyed hair-binding peptide is $10^{-5}$ M or less, preferably $10^{-6}$ M or less, more preferably $10^{-7}$ M or less, and most preferably $10^{-8}$ M or less.

Production of Binding Peptides

The binding peptides of the present invention may be prepared using standard peptide synthesis methods, which are well known in the art (see for example Stewart et al., *Solid Phase Peptide Synthesis*, Pierce Chemical Co., Rockford, Ill., 1984; Bodanszky, *Principles of Peptide Synthesis*, Springer-Verlag, New York, 1984; and Pennington et al., *Peptide Synthesis Protocols*, Humana Press, Totowa, N.J., 1994). Additionally, many companies offer custom peptide synthesis services.

Alternatively, the peptides of the present invention may be prepared using recombinant DNA and molecular cloning techniques. Genes encoding the dyed hair-binding peptides may be produced in heterologous host cells, particularly in the cells of microbial hosts.

Preferred heterologous host cells for expression of the binding peptides of the present invention are microbial hosts that can be found broadly within the fungal or bacterial families and which grow over a wide range of temperature, pH values, and solvent tolerances. Because transcription, translation, and the protein biosynthetic apparatus are the same irrespective of the cellular feedstock, functional genes are expressed irrespective of carbon feedstock used to generate cellular biomass. Examples of host strains include, but are not limited to, fungal or yeast species such as *Aspergillus, Trichoderma, Saccharomyces, Pichia, Candida, Yarrowia, Hansenula*, or bacterial species such as *Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*.

A variety of expression systems can be used to produce the peptides of the present invention. Such vectors include, but are not limited to, chromosomal, episomal and virus-derived vectors, e.g., vectors derived from bacterial plasmids, from bacteriophage, from transposons, from insertion elements, from yeast episomes, from viruses such as baculoviruses, retroviruses and vectors derived from combinations thereof such as those derived from plasmid and bacteriophage genetic elements, such as cosmids and phagemids. The expression system constructs may contain regulatory regions that regulate as well as engender expression. In general, any system or vector suitable to maintain, propagate or express polynucleotide or polypeptide in a host cell may be used for expression in this regard. Microbial expression systems and expression vectors contain regulatory sequences that direct high level expression of foreign proteins relative to the growth of the host cell. Regulatory sequences are well known to those skilled in the art and examples include, but are not limited to, those which cause the expression of a gene to be turned on or off in response to a chemical or physical stimulus, including the presence of regulatory elements in the vector, for example, enhancer sequences. Any of these could be used to construct chimeric genes for production of the any of the binding peptides of the present invention. These chimeric genes could then be introduced into appropriate microorganisms via transformation to provide high level expression of the peptides.

Vectors or cassettes useful for the transformation of suitable host cells are well known in the art. Typically the vector or cassette contains sequences directing transcription and translation of the relevant gene, one or more selectable markers, and sequences allowing autonomous replication or chromosomal integration. Suitable vectors comprise a region 5' of the gene, which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host. Selectable marker genes provide a phenotypic trait for selection of the transformed host cells such as tetracycline or ampicillin resistance in *E. coli*.

Initiation control regions or promoters which are useful to drive expression of the chimeric gene in the desired host cell are numerous and familiar to those skilled in the art. Virtually any promoter capable of driving the gene is suitable for producing the binding peptides of the present invention including, but not limited to: CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

The vector containing the appropriate DNA sequence is typically employed to transform an appropriate host to permit the host to express the peptide of the present invention. Cell-free translation systems can also be employed to produce such peptides using RNAs derived from the DNA constructs of the present invention. Optionally it may be desired to produce the instant gene product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the production host. Methods for choosing appropriate signal sequences are well known in the art (see for example EP 546049 and WO 9324631). The secretion signal DNA or facilitator may be located between the expression-controlling DNA and the instant gene or gene fragment, and in the same reading frame with the latter.

Hair Care Compositions

The benefit agent may include any compound or material that provides benefit to hair and typically includes, but is not limited to colorants, conditioners (include conditioning peptides), and sunscreen agents (for example, see U.S. Pat. Nos. 7,220,405; 7,060,260; and U.S. patent application Ser. Nos. 11/590,717; 11/074,473; 11/939,583 and 11/923,829). "Hair care compositions" are herein defined as compositions for the treatment of hair including, but not limited to, shampoos, conditioners, rinses, lotions, aerosols, gels, and mousses. An effective amount of the peptide-based hair reagent for use in hair care compositions is a concentration of about 0.001% to about 20%, preferably about 0.01% to about 5% by weight relative to the total weight of the composition. This proportion may vary as a function of the type of hair care composition. Additionally, the hair care composition may further comprise at least one pigment. The concentration of the peptide-based hair reagent in relation to the concentration of the pigment may need to be optimized for best results. Additionally, a mixture of different peptide-based hair reagents (used for coloring) having an affinity for different pigments may be used in the composition. The peptide-based hair coloring reagents in the mixture need to be chosen so that there is no interaction between the peptides that mitigates the beneficial effect. Suitable mixtures of peptide-based hair coloring reagents may be determined by one skilled in the art using routine experimentation. If a mixture of peptide-based hair coloring reagents is used in the composition, the total concentration of the reagents is about 0.01% to about 10% by weight relative to the total weight of the composition.

The composition may further comprise a cosmetically acceptable medium for hair care compositions, examples of which are described by Philippe et al. in U.S. Pat. No. 6,280, 747, and by Omura et al. in U.S. Pat. No. 6,139,851 and Cannell et al. in U.S. Pat. No. 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight for the aqueous-alcoholic solutions. Additionally, the hair care compositions may contain one or more conventional cosmetic or dermatological additives or adjuvants including, but not limited to, antioxidants, preserving agents, fillers, surfactants, UVA and/or UVB sunscreens, fragrances, thickeners, wetting agents and anionic, nonionic or amphoteric polymers, and dyes.

Hair Care Compositions: Peptide-Based Hair Conditioners

The peptide-based hair conditioners of the present invention are formed by coupling a dyed-hair-binding peptide (DHBP) with a hair conditioning agent (HCA). The dyed-hair-binding peptide part of the conditioner binds strongly to the dyed hair, thus keeping the conditioning agent attached to the dyed hair for a long lasting conditioning effect. The dyed-hair-binding peptides include the dyed-hair-binding peptide sequences of the invention, given by SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 29, 29, 30, 31, 32, 33 and 34.

Hair conditioning agents as herein defined are agents which improve the appearance, texture, and sheen of hair as well as increasing hair body or suppleness. Hair conditioning agents, include, but are not limited to, styling aids, hair straightening aids, hair strengthening aids, and volumizing agents, such as nanoparticles. In the peptide-based hair conditioners of the present invention, any known hair conditioning agent may be used. Hair conditioning agents are well known in the art, see for example Green et al. (WO 01/07009) and are available commercially from various sources. Suitable examples of hair conditioning agents include, but are not limited to, cationic polymers, such as cationized guar gum, diallyl quaternary ammonium salt/acrylamide copolymers, quaternized polyvinylpyrrolidone and derivatives thereof, and various polyquaternium-compounds; cationic surfactants, such as stearalkonium chloride, centrimonium chloride, and Sapamin hydrochloride; fatty alcohols, such as behenyl alcohol; fatty amines, such as stearyl amine; waxes; esters; nonionic polymers, such as polyvinylpyrrolidone, polyvinyl alcohol, and polyethylene glycol; silicones; siloxanes, such as decamethylcyclopentasiloxane; polymer emulsions, such as amodimethicone; and nanoparticles, such as silica nanoparticles and polymer nanoparticles. The preferred hair conditioning agents of the present invention contain amine or hydroxyl functional groups to facilitate coupling to the dyed-hair-binding peptides, as described below. Examples of preferred conditioning agents are octylamine (CAS No. 111-86-4), stearyl amine (CAS No. 124-30-1), behenyl alcohol (CAS No. 661-19-8, Cognis Corp., Cincinnati, Ohio), vinyl group terminated siloxanes, vinyl group terminated silicone (CAS No. 68083-19-2), vinyl group terminated methyl vinyl siloxanes, vinyl group terminated methyl vinyl silicone (CAS No. 68951-99-5), hydroxyl terminated siloxanes, hydroxyl terminated silicone (CAS No. 80801-30-5), amino-modified silicone derivatives, [(aminoethyl)amino]propyl hydroxyl dimethyl siloxanes, [(aminoethyl)amino]propyl hydroxyl dimethyl silicones, and alpha-tridecyl-omega-hydroxy-poly(oxy-1,2-ethanediyl) (CAS No. 24938-91-8).

The peptide-based hair conditioners of the present invention are prepared by coupling a specific dyed-hair-binding peptide to a hair conditioning agent, either directly or via an optional spacer. The coupling interaction may be a covalent bond or a non-covalent interaction, such as hydrogen bonding, electrostatic interaction, hydrophobic interaction, or Van der Waals interaction. In the case of a non-covalent interaction, the peptide-based hair conditioner may be prepared by mixing the peptide with the conditioning agent and the optional spacer (if used) and allowing sufficient time for the interaction to occur. The unbound materials may be separated from the resulting peptide-based hair conditioner adduct using methods known in the art, for example, gel permeation chromatography.

The peptide-based hair conditioners of the invention may also be prepared by covalently attaching a specific dyed-hair-binding peptide to a hair conditioning agent, either directly or through a spacer. Any known peptide or protein conjugation chemistry may be used to form the peptide-based hair conditioners of the present invention. Conjugation chemistries are well-known in the art (see for example, Hermanson, *Bioconjugate Techniques*, Academic Press, New York (1996)). Suitable coupling agents include, but are not limited to, carbodiimide coupling agents, diacid chlorides, diisocyanates and other difunctional coupling reagents that are reactive toward terminal amine and/or carboxylic acid terminal groups on the peptides and to amine, carboxylic acid, or alcohol groups on the hair conditioning agent. The preferred coupling agents are carbodiimide coupling agents, such as 1-ethyl-3-(3-dimethylaminopropyl)-carbodiimide (EDC) and N,N'-dicyclohexyl-carbodiimide (DCC), which may be used to activate carboxylic acid groups for coupling to alcohol, and amine groups. Additionally, it may be necessary to protect reactive amine or carboxylic acid groups on the peptide to produce the desired structure for the peptide-based hair conditioner. The use of protecting groups for amino acids, such as t-butyloxycarbonyl (t-Boc), are well known in the art (see for example Stewart et al., supra; Bodanszky, supra; and Pennington et al., supra). In some cases it may be necessary to introduce reactive groups, such as carboxylic acid, alcohol, amine, or aldehyde groups, on the hair conditioning agent for coupling to the dyed-hair-binding peptide. These modifications may be done using routine chemistry such as oxidation, reduction and the like, which is well known in the art.

It may also be desirable to couple the dyed-hair-binding peptide to the hair conditioning agent via a spacer. The spacer serves to separate the conditioning agent from the peptide to ensure that the agent does not interfere with the binding of the peptide to the hair. The spacer may be any of a variety of molecules, such as alkyl chains, phenyl compounds, ethylene glycol, amides, esters and the like. Preferred spacers are hydrophilic and have a chain length from 1 to about 100 atoms, more preferably, from 2 to about 30 atoms. Examples of preferred spacers include, but are not limited to ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl chains, and ethyl, propyl, hexyl, steryl, cetyl, and palmitoyl alkyl chains. The spacer may be covalently attached to the peptide and the hair conditioning agent using any of the coupling chemistries described above. In order to facilitate incorporation of the spacer, a bifunctional cross-linking agent that contains a spacer and reactive groups at both ends for coupling to the peptide and the conditioning agent may be used. Suitable bifunctional cross-linking agents are well known in the art and include, but are not limited to diamines, such a as 1,6-diaminohexane; dialdehydes, such as glutaraldehyde; bis N-hydroxysuccinimide esters, such as ethylene glycol-bis(succinic acid N-hydroxysuccinimide ester), disuccinimidyl glutarate, disuccinimidyl suberate, and ethylene glycol-bis(succinimidylsuccinate); diisocyanates, such as hexamethylenediisocyanate; bis oxiranes, such as 1,4 butanediyl diglycidyl ether; dicarboxylic acids, such as succinyldisalicylate; and the like. Heterobifunctional cross-linking agents, which contain a different reactive group at each end, may also be used. Examples of heterobifunctional cross-linking agents include, but are not limited to compounds having the following structure:

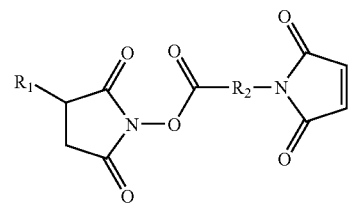

where: $R_1$ is H or a substituent group such as —$SO_3Na$, —$NO_2$, or —Br; and $R_2$ is a spacer such as —$CH_2CH_2$ (ethyl), —$(CH_2)_3$ (propyl), or —$(CH_2)_3C_6H_5$ (propyl phenyl). An example of such a heterobifunctional cross-linking agent is 3-maleimidopropionic acid N-hydroxysuccinimide ester. The N-hydroxysuccinimide ester group of these reagents reacts with amine or alcohol groups on the conditioner, while the maleimide group reacts with thiol groups present on the peptide. A thiol group may be incorporated into the peptide by adding a cysteine group to at least one end of the binding peptide sequence (i.e., the C-terminus or N-terminus). Several spacer amino acid residues, such as glycine, may be incorporated between the binding peptide sequence and the terminal cysteine to separate the reacting thiol group from the binding sequence.

Additionally, the spacer may be a peptide composed of any amino acid and mixtures thereof. The preferred peptide spacers are composed of the amino acids glycine, alanine, and serine, and mixtures thereof. In addition, the peptide spacer may contain a specific enzyme cleavage site, such as the protease Caspase 3 site, given by SEQ ID NO: 38, which allows for the enzymatic removal of the conditioning agent from the hair. The peptide spacer may be from 1 to about 50 amino acids, preferably from 1 to about 20 amino acids. These peptide spacers may be linked to the binding peptide sequence by any method known in the art. For example, the entire binding peptide-peptide spacer diblock may be prepared using the standard peptide synthesis methods described supra. In addition, the binding peptide and peptide spacer blocks may be combined using carbodiimide coupling agents (see for example, Hermanson, *Bioconjugate Techniques*, Academic Press, New York (1996)), diacid chlorides, diisocyanates and other difunctional coupling reagents that are reactive to terminal amine and/or carboxylic acid terminal groups on the peptides. Alternatively, the entire binding peptide-peptide spacer diblock may be prepared using the recombinant DNA and molecular cloning techniques described supra. The spacer may also be a combination of a peptide spacer and an organic spacer molecule, which may be prepared using the methods described above.

It may also be desirable to have multiple dyed-hair-binding peptides coupled to the hair conditioning agent to enhance the interaction between the peptide-based hair conditioner and the hair. Either multiple copies of the same dyed-hair-binding peptide or a combination of different dyed-hair-binding peptides may be used. In the case of large conditioning particles (e.g., particle emulsions), a large number of dyed-hair-binding peptides, i.e., up to about 1,000, may be coupled to the conditioning agent. A smaller number of dyed-hair-binding peptides can be coupled to the smaller conditioner molecules, i.e., up to about 50. Therefore, in one embodiment of the present invention, the peptide-based hair conditioners are diblock compositions consisting of a dyed-hair-binding peptide (DHBP) and a hair conditioning agent (HCA), having the general structure $(DHBP)_n$—HCA, where n ranges from 1 to about 1,000, preferably from 1 to about 50; wherein the dyed-hair-binding peptide is selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 29, 29, 30, 31, 32, 33 and 34. In another embodiment, the peptide-based hair conditioners contain a spacer (S) separating the dyed-hair-binding peptide from the hair conditioning agent, as described above. Multiple copies of the dyed-hair-binding peptide may be coupled to a single spacer molecule. In this embodiment, the peptide-based hair conditioners are triblock compositions consisting of a dyed-hair-binding peptide, a spacer, and a hair conditioning agent, having the general structure $[(DHBP)_m-S]_n-HCA$, where n ranges from 1 to about 1,000, preferably n is 1 to about 50, and m ranges from 1 to about 50, preferably m is 1 to about 10.

It should be understood that as used herein, DHBP is a generic designation referring to any one of the present dyed-hair-binding peptides described herein. Where n or m as used above, is greater than 1, it is well within the scope of the invention to provide for the situation where a series of dyed-hair-binding peptides of different sequences may form a part of the composition. Additionally, it should be understood that these structures do not necessarily represent a covalent bond between the peptide, the hair conditioning agent, and the optional spacer. As described above, the coupling interaction between the peptide, the hair conditioning agent, and the optional spacer may be either covalent or non-covalent.

The peptide-based hair conditioners of the present invention may be used in compositions for hair care. It should also be recognized that the dyed-hair-binding peptides themselves can serve as conditioning agents for the treatment of hair. Hair care compositions are herein defined as compositions for the treatment of hair, including but not limited to shampoos, conditioners, lotions, aerosols, gels, mousses, and hair dyes comprising an effective amount of a peptide-based hair conditioner or a mixture of different peptide-based hair conditioners in a cosmetically acceptable medium. In one embodiment, the hair care compositions are compositions for the treatment of dyed hair. An effective amount of a peptide-based hair conditioner or dyed-hair-binding peptide for use in a hair care composition is herein defined as a proportion of from about 0.001% to about 20%, preferably 0.01 to 10%, and most preferably about 0.01% to about 5% by weight relative to the total weight of the composition. Components of a cosmetically acceptable medium for hair care compositions are described by Philippe et al. in U.S. Pat. No. 6,280,747, and by Omura et al. in U.S. Pat. No. 6,139,851 and Cannell et al. in U.S. Pat. No. 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants including but not limited to, antioxidants, preserving agents, fillers, surfactants, UVA and/or UVB sunscreens, fragrances, thickeners, wetting agents and anionic, nonionic or amphoteric polymers, and dyes or pigments.

Hair Care Compositions: Peptide-Based Hair Colorants

The peptide-based hair colorants of the present invention are formed by coupling at least one of the present dyed-hair-binding peptides (DHBP) with a coloring agent (C). The dyed-hair-binding peptide part of the peptide-based hair colorant binds strongly to the hair, thus keeping the coloring agent attached to the hair for a long lasting hair coloring effect. The dyed-hair-binding peptides are selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 29, 29, 30, 31, 32, 33 and 34. Additionally, any known normal hair-binding peptide (i.e. peptides that bind to non-dyed hair) may be used in combination with one or more of the present dyed-hair-binding peptides, including those described by Janssen et al. in U.S. Patent Application Publication No. 2003/0152976 and by Janssen et al. in WO 04048399, respectively.

Coloring agents as herein defined are any dye, pigment, lake, and the like that may be used to change the color of hair. In the peptide-based hair colorants of the present invention, any known coloring agent may be used. Hair coloring agents are well known in the art (see for example Green et al. supra, *CFTA International Color Handbook*, $2^{nd}$ ed., Micelle Press, England (1992) and *Cosmetic Handbook*, US Food and Drug Administration, FDA/IAS Booklet (1992)), and are available commercially from various sources (for example Bayer, Pittsburgh, Pa.; Ciba-Geigy, Tarrytown, N.Y.; ICI, Bridgewater, N.J.; Sandoz, Vienna, Austria; BASF, Mount Olive, N.J.; and Hoechst, Frankfurt, Germany).

Hair dyes are well-known in the art and may include any cosmetically acceptable organic, inorganic, natural, or synthetic dye, including mixtures thereof. Examples of dyes include, but are not limited to 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, 2-nitro-5-glyceryl methylaniline, 3-methylamino-4-nitrophenoxyethanol, 3-nitro-p-hydroxyethylaminophenol, hydroxyanthraquinoneaminopropylmethyl morpholinium methosulfate, Henna, HC Blue 1, HC Blue 2, HC Yellow 4, HC Red 3, HC Red 5, HC Red 7, HC Violet 1, HC Violet 2, HC Blue 7, HC Blue 10, HC Blue 12, HC Yellow 2, HC Yellow 6, HC Yellow 8, HC Yellow 12, HC Orange 2, HC Orange 3, HC Brown 2, D&C Yellow 1, D&C Yellow 3, D&C Blue 1, Disperse Blue 3, Disperse Violet 1, Disperse Orange, Disperse Violet 4, Disperse Black 9, Basic Orange 31, Basic Yellow 57, Basic Yellow 87, HC Yellow No. 9, Basic Blue 26, Basic Blue 7, Basic Blue 99, Basic Violet 14, Basic Violet 2, Basic Brown 16, Basic Brown 17, Basic Red 2, Basic Red 51, Basic Red 76, Acid Red 33, Acid Violet 43, Brilliant Black 1, eosin derivatives, halogenated fluorescein derivatives and dihydroxyacetone. In another embodiment, the dye is selected form the group consisting of Basic Brown 16, Basic Brown 17, Basic Red 2, Basic Red 76, Basic Blue 99, Basic Yellow 57, Basic Red 51, Acid Violet 43, Basic Yellow 57, and mixtures thereof. In a preferred embodiment, the dye is a cationic semi-permanent dye (for example, see those described in U.S. Pat. Nos. 6,506,374 and 7,060,113; hereby incorporated by reference). In a further embodiment, the dye is Basic Brown 17, also known as Arianor Sienna Brown.

Pigments are also suitable benefit agents of the invention and include, but are not limited to D&C Red No. 36 and D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, titanium dioxide nanoparticles, zinc oxide, barium oxide, ultramarine blue, bismuth citrate, and carbon black particles. The preferred hair coloring agents of the present invention are D&C Yellow 1 and 3, HC Yellow 6 and 8, D&C Blue 1, HC Blue 1, HC Brown 2, HC Red 5, 2-nitro-paraphenylenediamine, N,N-hydroxyethyl-2-nitro-phenylenediamine, 4-nitro-indole, and carbon black.

Metallic and semiconductor nanoparticles may also be used as hair coloring agents due to their strong emission of light (Vic et al. U.S. Patent Application Publication No. 2004/0010864). The metallic nanoparticles include, but are not limited to, particles of gold, silver, platinum, palladium, iridium, rhodium, osmium, iron, copper, cobalt, and alloys composed of these metals. An "alloy" is herein defined as a homogeneous mixture of two or more metals. The "semiconductor nanoparticles" include, but are not limited to, particles of cadmium selenide, cadmium sulfide, silver sulfide, cadmium sulfide, zinc oxide, zinc sulfide, zinc selenide, lead sulfide, gallium arsenide, silicon, tin oxide, iron oxide, and indium phosphide. The nanoparticles are stabilized and made water-soluble by the use of a suitable organic coating or monolayer. As used herein, monolayer-protected nanoparticles are one type of stabilized nanoparticle. Methods for the preparation of stabilized, water-soluble metal and semiconductor nanoparticles are known in the art, and are described by Huang et al. in co-pending U.S. patent application Ser. No. 10/622,889. The color of the nanoparticles depends on the size of the particles. Therefore, by controlling the size of the nanoparticles, different colors may be obtained. For example, ZnS-coated CdSe nanoparticles cover the entire visible spectrum over a particle size range of 2 to 6 nm. Specifically, CdSe nanoparticles with a core size of 2.3, 4.2, 4.8 and 5.5 nm emit light at the wavelength centered around 485, 565, 590, and 625 nm, respectively. Water-soluble nanoparticles of different sizes may be obtained from a broad size distribution of nanoparticles using the size fractionation method described by Huang, supra. That method comprises the regulated addition of a water-miscible organic solvent to a solution of nanoparticles in the presence of an electrolyte. Increasing additions of the water-miscible organic solvent result in the precipitation of nanoparticles of decreasing size. The metallic and semiconductor nanoparticles may also serve as volumizing agents, as described above.

Of particular utility are titanium dioxide nanoparticles that not only serve as a colorant but additionally may serve to block harmful UV radiation (i.e. "a sunscreen agent"). Suitable titanium dioxide nanoparticles are described in U.S. Pat. Nos. 5,451,390; 5,672,330; and 5,762,914. Titanium dioxide P25 is an example of a suitable commercial product available from Degussa. Other commercial suppliers of titanium dioxide nanoparticles include Kemira, Sachtleben, and Tayca.

The titanium dioxide nanoparticles typically have an average particle size diameter of less than 100 nanometers (nm) as determined by dynamic light scattering which measures the particle size distribution of particles in liquid suspension. The particles are typically agglomerates which may range from about 3 nm to about 6000 nm. Any process known in the art can be used to prepare such particles. The process may involve vapor phase oxidation of titanium halides or solution precipitation from soluble titanium complexes, provided that titanium dioxide nanoparticles are produced.

A preferred process to prepare titanium dioxide nanoparticles is by injecting oxygen and titanium halide, preferably titanium tetrachloride, into a high-temperature reaction zone, typically ranging from 400 to 2000 degrees centigrade. Under the high temperature conditions present in the reaction zone, nanoparticles of titanium dioxide are formed having high surface area and a narrow size distribution. The energy source in the reactor may be any heating source such as a plasma torch.

Additionally, the coloring agent may be a colored, polymeric microsphere. Exemplary polymeric microspheres include, but are not limited to, microspheres of polystyrene, polymethylmethacrylate, polyvinyltoluene, styrene/butadiene copolymer, and latex. For use in the invention, the microspheres have a diameter of about 10 nanometers to about 2 microns. The microspheres may be colored by coupling any suitable dye, such as those described above, to the microspheres. The dyes may be coupled to the surface of the microsphere or adsorbed within the porous structure of a porous microsphere. Suitable microspheres, including undyed and dyed microspheres that are functionalized to enable covalent attachment, are available from companies such as Bang Laboratories (Fishers, Ind.).

The peptide-based hair colorants of the present invention are prepared by coupling at least one of the present dyed-hair-binding peptides to a coloring agent, either directly or via a spacer. Any of the coupling methods described above may be used. It may be necessary to introduce reactive groups, such as carboxylic acid, alcohol, amine, or aldehyde groups, on the coloring agent for coupling to the dyed-hair-binding peptide. These modifications may be done using routine chemistry, which is well known in the art. For example, the surface of carbon black particles may be oxidized using nitric acid, a peroxide such as hydrogen peroxide, or an inorganic initiator such as ammonium persulfate, to generate functional groups. Preferably, the carbon black surface is oxidized using ammonium persulfate as described by Carrasco-Marin et al. (*J. Chem. Soc., Faraday Trans.* 93:2211-2215 (1997)). Amino functional groups may be introduced to the surface of carbon black using an organic initiator such as 2,2'-Azobis(2-methylpropionamide)-dihydrochloride. The inorganic pigments and the nanoparticles may be derivatized to introduce carboxylic acid or amino functional groups in a similar manner.

Additionally, the dyed-hair-binding peptide may be coupled to a pigment using a pigment-binding peptide (e.g., for color enhancement). Suitable pigment-binding peptide sequences are known in the art. For example, Nomoto et al. in EP1275728 describe peptides that bind to carbon black, copper phthalocyanine, titanium dioxide, and silicon dioxide. O'Brien et al. in co-pending and commonly owned U.S. patent application Ser. No. 10/935,254 describe peptides that bind to carbon black, Cromophtal® Yellow, Sunfast® Magenta, and Sunfast® Blue. Additional pigment-binding peptides may be identified using the any of the screening methods described above. The pigment-binding peptide may be coupled to the dyed-hair-binding peptide either directly or through a spacer using any of the coupling methods described above. The dyed-hair-binding peptide-pigment binding peptide diblock or triblock (if a spacer is used) is contacted with the pigment to attach it to the pigment-binding peptide.

It may also be desirable to have multiple dyed-hair-binding peptides coupled to the coloring agent to enhance the interaction between the peptide-based hair colorant and the hair. Either multiple copies of the same dyed-hair-binding peptide or a combination of different dyed-hair-binding peptides may be used. In the case of large pigment particles, a large number of dyed-hair-binding peptides, i.e., up to about 10,000, may be coupled to the pigment. A smaller number of dyed-hair-binding peptides can be coupled to the smaller dye molecules, i.e., up to about 50. Therefore, in one embodiment of the present invention, the peptide-based hair colorants are diblock compositions consisting of at least one of the present dyed-hair-binding peptides (DHBP) and a coloring agent (C), having the general diblock structure $(DHBP)_n$—C, where n ranges from 1 to about 1,000, preferably n is 1 to about 500.

In another embodiment, the peptide-based hair colorants contain a spacer (S) separating the binding peptide from the hair coloring agent, as described above. Multiple copies of the dyed-hair-binding peptide may be coupled to a single spacer molecule. In this embodiment, the peptide-based hair colorants are triblock compositions consisting of at least one of the present dyed-hair-binding peptides, a spacer, and a coloring agent, having the general structure [(DHBP)$_m$—S]$_n$—C, where n ranges from 1 to about 1,000, preferably n is 1 to about 500, and m ranges from 1 to about 50, preferably m is 1 to about 10, and S is a spacer.

It should be understood that as used herein, DHBP is a generic designation for the present dyed-hair-binding peptides. Where n or m as used above, is greater than 1, it is well within the scope of the invention to provide for the situation where a series of dyed-hair-binding peptides of different sequences may form a part of the composition. Additionally, it should be understood that these structures do not necessarily represent a covalent bond between the peptide, the coloring agent, and the optional spacer. As described above, the coupling interaction between the peptide, the coloring agent, and the optional spacer may be either covalent or non-covalent.

The peptide-based hair colorants of the present invention may be used in hair coloring compositions for dyeing hair for enhancing the color or appearance of previously dyed hair. Hair coloring compositions are herein defined as compositions for the coloring, dyeing, or bleaching of hair, comprising an effective amount of peptide-based hair colorant or a mixture of different peptide-based hair colorants in a cosmetically acceptable medium. An effective amount of a peptide-based hair colorant for use in a hair coloring composition is herein defined as a proportion of from about 0.001% to about 20% by weight relative to the total weight of the composition. Components of a cosmetically acceptable medium for hair coloring compositions are described by Dias et al., in U.S. Pat. No. 6,398,821 and by Deutz et al., in U.S. Pat. No. 6,129,770. For example, hair coloring compositions may contain sequestrants, stabilizers, thickeners, buffers, carriers, surfactants, solvents, antioxidants, polymers, and conditioners. The conditioners may include the peptide-based hair conditioners and dyed-hair-binding peptides of the present invention in a proportion from about 0.001% to about 20%, preferably 0.01% to about 10%, most preferably about 0.01% to about 5% by weight relative to the total weight of the hair coloring composition.

In another embodiment, the peptide-based hair colorants of the present invention may also be used as coloring agents in cosmetic compositions that are applied to the eyelashes or eyebrows including, but not limited to mascaras, and eyebrow pencils. These may be anhydrous make-up products comprising a cosmetically acceptable medium which contains a fatty substance in a proportion generally of from about 10 to about 90% by weight relative to the total weight of the composition, where the fatty phase containing at least one liquid, solid or semi-solid fatty substance, as described above. The fatty substance includes, but is not limited to, oils, waxes, gums, and so-called pasty fatty substances. Alternatively, these compositions may be in the form of a stable dispersion such as a water-in-oil or oil-in-water emulsion, as described above. In these compositions, the proportion of the peptide-based hair colorant is generally from about 0.001% to about 20% by weight relative to the total weight of the composition.

Methods for Treating Hair

In another embodiment, methods are provided for treating dyed hair with the peptide-based conditioners and colorants of the present invention. Specifically, the present invention also comprises a method for forming a protective film of peptide-based conditioner on dyed hair by applying one of the compositions described above comprising an effective amount of a peptide-based hair conditioner to the dyed hair and allowing the formation of the protective film. The compositions of the present invention may be applied to dyed hair by various means, including, but not limited to spraying, brushing, and applying by hand. The peptide-based conditioner composition is left in contact with dyed hair for a period of time sufficient to form the protective film, preferably for at least about 0.1 min to 60 min.

The present invention also provides a method for coloring dyed hair (including color enhancement of previously dyed hair) by applying a hair coloring composition comprising an effective amount of a peptide-based hair colorant to the dyed hair by means described above. The hair coloring composition is allowed to contact the dyed hair for a period of time sufficient to cause coloration of the dyed hair, preferably between about 5 seconds to about 50 minutes, and more preferably from about 5 seconds to about 60 seconds, and then the hair coloring composition may be rinsed from the dyed hair.

The above methods of application of the binding reagents to dyed hair surfaces are characterized by the ability of the reagent to bind to a surface in an aqueous environment and to bind rapidly, often within 5 seconds to about 60 seconds from the time of first application. The reagents of the invention are multifaceted bio-adhesives with a multiplicity of applications but unified in their water fast nature and rapid and tight binding characteristics.

Unless otherwise noted, all cited U.S. patents, patent applications, and patent application publications are hereby incorporated by reference in their entirety.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "sec" means second(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "mM" means millimolar, "µM" means micromolar, "M" means molar, "mmol" means millimole(s), "µmole" means micromole(s), "g" means gram(s), "µg" means microgram(s), "mg" means milligram(s), "g" means the gravitation constant, "rpm" means revolutions per minute, "pfu" means plaque forming unit, "BSA" means bovine serum albumin, "ELISA" means enzyme linked immunosorbent assay, "A" means absorbance, "$A_{450}$" means the absorbance measured at a wavelength of 450 nm, "$A_{405}$" means the absorbance measured at a wavelength of 405 nm, "$OD_{600}$" means optical density measured at 600 nm, "TBS" means Tris-buffered saline, "TBST" means Tris-buffered saline plus TWEEN®20 (at a specified concentration); "SEM" means standard error of the mean, "ESCA" means electron spectroscopy for chemical analysis, "eV" means electron volt(s), "TGA" means thermogravimetric analysis, "GPC" means gel permeation chromatography, "MW" means molecular weight, "$M_w$" means weight-average molecular weight, "vol %" means volume percent, "NMR" means nuclear magnetic resonance spectroscopy, and "MALDI mass spectrometry" means matrix assisted, laser desorption ionization mass spectrometry.

General Methods:

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989. All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Phage Display Peptide Libraries:

Several combinatorial libraries of random peptides of various lengths (phage displayed peptide inserts averaged from about 7 to about 17 amino acids in length) fused to a minor coat protein (pIII) of M13 phage were used. The displayed peptide is expressed at the N-terminus of pill, such that after the signal peptide is cleaved, the first residue of the coat protein is the first residue of the displayed peptide.

Preparation of Dyed Hair

An aqueous solution (0.5%) of Arianor Sienna Brown (Basic Brown 17), containing 3% benzyl alcohol and 0.05% diazolidinyl urea (biocide) was prepared. The dye solution had a pH of 4.4. This was divided into two equal volumes, one at the original acidic pH, and the other is adjusted to a pH between 8.5-9.0, using ethanolamine.

Bundles (one inch long) of natural white hair (International Hair Importers and Products, Bellerose, N.Y.) were immersed in the acidic or basic dye solutions for 30 minutes, water rinsed, and then air dried overnight. The tresses were then cut into individual sections weighing 30-75 mg each.

Example 1

Selection of Dyed-Hair-Binding Phage Peptides Using Standard Biopanning

The purpose of this Example was to identify dyed-hair-binding phage peptides that bind to dyed hair using standard phage display biopanning. The hair used was natural white (piedmont white) human hair obtained from (International Hair Importers and Products (Bellerose, N.Y.) that were dyed with a semi-permanent cationic dye (Basic Brown 17; also referred to as Arianor Sienna Brown by the manufacturer).

A wad of hair (approximately 20 to 40 strands, each about 10 cm long) was placed in each well (23 wells used, each well comprising a different phage display library) of a deep well plate (e.g., 96 wells, 2 mL/per well capacity). Non-specific binding sites were blocked by wetting the hair and the surface of the wells with 1.5 mL of 10% bovine serum albumin (BSA) in Tris-buffered saline ("buffer-T" or "TBS"). The plate was incubated for 1 hour at room temperature (approximately 22° C.) with shaking at 50 rpm. The liquid was aspirated from each well.

Approximately 0.5 mL of blocking reagent (10% BSA in TBS) was added to each well. Then 25 µL of the phage library diluted in buffer-T (100 µL) (phage displayed peptide inserts averaged from about 7 to about 17 amino acids in length) was added to each well at a concentration of $10^{10}$ pfu/mL. After 30 minutes of incubation at room temperature and shaking at 50 rpm, unbound phage were removed by aspirating the liquid from each well followed by 6 washes with 1.1 mL TBS containing the detergent TWEEN® 20 (a.k.a "TBST") at a final concentration of 0.05%. The final wash also included shaking at 50 rpm at room temperature for 20 minutes prior to aspiration of the washing buffer.

*E. coli* cells ER2738 (susceptible to phage infection in 2×YT media; commercially available from New England BIOLABS®, Ipswich, Mass.), previously diluted 1:100 prior to overnight growth in 2×YT media with tetracycline (10 µg/mL) were diluted to ~0.025 $OD_{600nm}$ (e.g., 120 µL of OD 3 culture plus 13.88 mL media). Approximately 500 µL of diluted cells (10E8) were added to each well containing phage. The cells were then incubated for 30 minutes at 37° C. without shaking. The cells were then incubated for an additional 30 minutes at room temperature with shaking.

The media and bacterial cells were removed and used to inoculate 0.5 mL 2×YT plus tetracycline (10 µg/mL) (×23 wells) in a 96-well deep block. The cells were incubated overnight at 37° C. in an angled shaker.

The next day, phage supernatant was harvested by centrifugation at 8500×g for 10 minutes. Second and third rounds of selection were performed in a similar manner to the first round, using the amplified phage from the previous round as input (~100 µL of supernatant). Three or four selection rounds were used.

Each selection round was monitored for enrichment of phage displaying dyed-hair-binding peptides using ELISA-like assays in the deep well plates performed using an anti-M13 phage antibody conjugated to horseradish-peroxidase, followed by the addition of a chromogenic agent ABTS (2,2'-azino-bis(3-ethylbenzthiazoline-6-sulphonic acid)). The plates were read at 405 nm.

Libraries that showed enrichment of phage displaying hair-binding peptides were plated on a lawn of *E. coli* cells (DH5α; New England BIOLABS®), and individual plaques were picked and tested for binding to dyed hair. Relative binding strengths of the phage can also be determined by testing serial dilutions of the phage for binding to dyed hair in an ELISA. For example, serial dilutions of the display-selected clones were exposed to dyed hair in an ELISA. The higher dilutions represent more stringent assays for affinity; therefore, phage that yield a signal at higher dilutions represent peptides with higher relative affinity for dyed hair as a substrate. Primers against the phage vector sequence (available from New England BIOLABS®) that flank the insertion site were used to determine the DNA sequence encoding the peptide for the phage in each group. The sequence encoding the peptide insert was translated to yield the corresponding amino acid sequence displayed on the phage surface. Similar procedures were used to develop hair-binding peptides that have binding specificity for a substrate comprising hair, wherein the hair had been dyed using a commercial hair coloring product. The DNA sequences encoding dyed-hair-binding peptides isolated were determined. The amino acid sequences of the dyed-hair-binding peptides were determined and are provided in Table 1. Peptides Dye-1 through Dye-16 were those sequenced after round 4 of selection. Peptides Dye 17 through Dye-28 were those isolated and sequenced after a fifth round of selection.

TABLE 1

Amino Acid Sequences of Eluted Dyed-Hair-Binding Phage Peptides

| Peptide ID No. | Amino Acid Sequence[1] | SEQ ID NO: |
|---|---|---|
| Dye-1 | ssNYNYNYNYQYSsr | 1 |
| Dye-2 | ssLLSDFHYGDMWDAsr | 2 |
| Dye-3 | ssSSNDSNVSWFHYYASGLTSsr | 3 |
| Dye-4 | ssSSLDFFSYSAFSGGVAEsr | 4 |
| Dye-5 | ssSSADAAYGHCCGAGFSTFSsr | 5 |
| Dye-6 | ssSSDVHNSIIGWDFYHSRGSsr | 6 |
| Dye-7 | ssSCYDVECSSFVAWMRGPSSsr | 7 |
| Dye-8 | ssYYNYHYQYQDSsr | 8 |
| Dye-9 | ssLFNMYGHQSVLGPsr | 9 |
| Dye-10 | ssFSVNEPHAWMAPLsr | 10 |
| Dye-11 | ssFSWVYGHGGLGFAsr | 11 |
| Dye-12 | ssFVSWSPYKSPPELsr | 12 |
| Dye-13 | ssGSVAVSAEASWFSGVAAsr | 13 |
| Dye-14 | ssFYGSSAFVSSGVSVAYGsr | 14 |
| Dye-15 | ssHYYYNDYDHQSsr | 15 |
| Dye-16 | ssLFSDVHYGSNKALsr | 16 |
| Dye-17 | ssSFAYLVPDDGWLSsr | 17 |
| Dye-18 | ssSCMGSHNPRMSVEESTRNCsr | 18 |
| Dye-19 | ssSCNNNWFYSSTLPGGDHACsr | 19 |
| Dye-20 | ssSGAVFSSGGADAGWGVWsr | 20 |
| Dye-21 | ssSFAASSAFSFLVDAVAWsr | 21 |
| Dye-22 | ssVDYEVPLAVAAEWGFSVsr | 22 |
| Dye-23 | ssADFASFGFFGFSAASADsr | 23 |
| Dye-24 | ssFAEAWSRAWPRAEVFFPSRGY | 24 |
| Dye-25 | ssHDEHYQYHYYSsr | 25 |
| Dye-26 | ssYYYDYYQQDYSsr | 26 |
| Dye-27 | ssQYYQDYQYYHSsr | 27 |
| Dye-28 | ssYHYDYDHYYESsr | 28 |

[1] = The ss (serine-serine) and sr (serine-arginine) at the N-terminus and C-terminus of each peptide are derived from the phage display vector, respectively.

Peptides Dye-1, Dye-2, Dye-3, Dye-26, Dye-27, and Dye-28 were submitted for peptide synthesis where a linker was added for the attachment of biotin. An additional sequence (AFF15025; SEQ ID NOs. 35 and 36) was prepared by fusing a (non-dyed) hair-binding peptide with a dyed-hair-binding peptide. The fused domains were separated by a short linker.

TABLE 2

Peptides synthesized.

| Peptide ID No. | Amino acid Sequence[a] (SEQ ID NO.) | Description |
|---|---|---|
| Aff15011 | NYNYNYNYQYSSR-GSSGK (biotin) (SEQ ID NO: 29) | Dye-1 with linker |
| Aff15013 | SSNDSNVSWFHYYASGLTSSR-GSSGK-(biotin) (SEQ ID NO: 30) | Dye-3 with linker |
| Aff15016 | LLSDFHYGDMWDASR-GSSGK (biotin) (SEQ ID NO: 31) | Dye-2 with linker |
| Aff15027 | YYYDYYQQDYSSR-GSSGK (biotin) (SEQ ID NO: 32) | Dye-26 with linker |
| Aff15029 | QYYQDYQYYHSSR-GSSK (biotin) (SEQ ID NO: 33) | Dye-27 with linker |
| Aff15030 | YHYDYDHYYESSR-GSSGK (biotin) (SEQ ID NO: 34) | Dye-28 with linker |
| Aff15025 | SSNDSNVSWFHYYASGLTSSR-GSSG-SRKSSQKNPHHPKPPKKPTAR-GSSGK (biotin) (SEQ ID NO: 35 and 36)[b] | Fusion of normal hair-binding peptide (AFF15014; underlined) with dyed hair-binding peptide (AFF15013) |

[a] = A GSSGK linker (SEQ ID NO: 37) was added to the sequences to facility linkage to biotin.
[b] = Two sequences are provided, SEQ ID NO: 35 is the fusion sequence without the biotin linker and SEQ ID NO: 36 is the sequence including the GSSGK linker.

Example 2

Characterization of Peptides for Dyed-Hair-Binding Activity

The ELISA-type assay described in Example 1 was used to evaluate the affinity of dyed-hair-binding peptides for dyed hair. All of the synthesize peptides in Table 2 were evaluated for their ability to bind to dyed hair versus two negative controls (a non-selected peptide and a blank (no peptide)). All of the sequences in Table 2 exhibited the ability to bind to dyed hair.

The $EC_{50}$ values (the concentration at which half the maximum binding was observed by measuring $A_{405\ nm}$) were deduced and given in Table 3.

TABLE 3

Calculated $EC_{50}$ values

| Peptide ID No. | $EC_{50}$ (concentration) |
|---|---|
| Aff15011 | >10 μM |
| Aff15013 | ~1 μM |
| Aff15016 | ~1 μM |
| Aff15027 | ~1 μM |
| Aff15029 | ~1 μM |
| Aff15030 | ~1 μM |
| Aff15025 | ~25 nM |

Example 3

Minitress Procedure for Evaluation of Peptides for Dye Enhancement

The purpose of this Example was to evaluate dyed-hair-binding peptides for their ability to enhance color retention for dyed hair.

A 0.5% aqueous solution of Arianor Sienna Brown (Basic Brown 17; Sensient Technologies Corp, Milwaukee, Wis.), containing 3% benzyl alcohol and 0.05% diazolidinyl urea (biocide) was prepared. The dye solution has a pH of 4.4. This was divided into two equal volumes, one at the original acidic pH, and the other was adjusted to a pH of 8.5-9.0, using ethanolamine.

Bundles (one inch long) of natural white hair were immersed in the acidic or basic dye solutions for 30 minutes, water rinsed, and then air dried overnight. The tresses were then cut into individual sections weighing 30-75 mg each.

Aqueous peptide solutions, varying in concentration, were neutralized with ethanolamine to pH 4.5-5.0 or made slightly basic (pH 8.5-9.0) as was the 3% benzyl alcohol diluent solutions Various loadings of target peptide and diluent were added to each well of a 24-well plate. Controls without peptide were run along side using the appropriate pH adjusted diluent. After mixing the components, a small dyed hair tress was added to each well and these were stirred for 30 minutes in the well. When stirring was completed, the hair tresses were removed, rinsed with distilled water, dried and colorimetric readings were taken using a spectrophotometer. Hair tresses were reinserted into the corresponding well containing beads for embrocation/mixing, and 2.5 mL of aqueous 50% shampoo (Pantene Pro V; Proctor and Gamble, Cincinnati, Ohio) was added. The well plate was agitated on an orbital shaker for 5-15 minute cycles to simulate shampoo embrocation through multiple cycles. The time and number of cycles were adjusted to achieve an equivalent of 12 manual shampoo treatments. The hair tresses were then rinsed with distilled water and dried. Colorimetric data for color loss was compiled and plotted along with peptide free controls. Delta E differences are then reported relative to the as dyed hair without peptide present.

The color intensity after the water rinse was measured using a X-Rite® SP78™ Sphere Spectrophotometer (X-Rite, Inc., Grandville, Mich.), by placing the colored hair sample into the photosensor and calculating L*, a* and b* parameters representing the photometer response. Initial baseline L*, a, b values were measured for the dyed-hair and all measurements were the average of five individual determinations. Delta E values were calculated using equation 1 below:

$$\text{Delta } E = ((L^*_1 - L^*_2)^2 + (a_1 - a_2)^2 + (b_1 - b_2)^2)^{1/2} \quad (1)$$

where L*=the lightness variable and a* and b* are the chromaticity coordinates of CIELAB colorspace as defined by the International Commission of Illumination (CIE) (Minolta, *Precise Color Communication—Color Control From Feeling to Instrumentation*, Minolta Camera Co., 1996). Larger Delta E difference values are indicative of better color retention. The results are summarized in Table 4. A negative value or zero would indicate a detrimental effect or no effect respectively in the presence of peptide.

TABLE 4

| Peptide ID No. | mg/mL peptide | Basic pH | Delta E difference | mg/mL peptide | Acidic pH | Delta E difference |
|---|---|---|---|---|---|---|
| Dye-1 (SEQ ID NO: 1) | — | — | — | 0.4 | pH 3.87 | 14 |
| Dye-1 (SEQ ID NO: 1) | 2 | pH 9.0 | 6.8 | — | — | — |
| Dye-1 (SEQ ID NO: 1) | 2 | pH 8.9 | 6.42 | 0.4 | pH 3.9 | 8.75 |
| Dye-24 (SEQ ID NO: 24) | 2 | pH 9.0 | 3.74 | — | — | — |
| Dye-26 (SEQ ID NO: 26) | 1 | pH 9.0 | 4.6 | — | — | — |
| Dye-26 (SEQ ID NO: 26) | 2 | pH 8.7 | 5.08 | 0.4 | pH 4.2 | 9.06 |
| Dye-17 (SEQ ID NO: 17) | 1 | pH 8.75 | 2.83 | — | — | — |

Prophetic Examples 4-10

Prophetic Examples 4-6 and 8-10 followed the procedures described in co-pending U.S. Pat. No. 7,220,405; U.S. patent application Ser. No. 11/074,473 (U.S. Patent Publication No. 2005/0226839) incorporated herein by reference. Prophetic Example 7 follows the procedures previously described in co-pending U.S. patent application Ser. No. 11/512,910 (corresponding to U.S. Patent Application Publication No. 2007/0067924), incorporated herein by reference.

Example 4 (Prophetic)

Determination of the Peptide Dyed-Hair-Binding Affinities

The purpose of this Example is to describe how to determine the affinity of the dyed-hair-binding peptides for dyed hair surfaces, measured as $MB_{50}$ values, using an ELISA assay.

Dyed-hair-binding peptides as described herein are synthesized using standard solid phage synthesis method and are biotinylated by adding a C-terminal linker (SEQ ID NO: 37) comprising a biotinylated lysine residue at the C-terminus of the amino acid binding sequence for detection purposes.

The $MB_{50}$ measurements of the biotinylated peptide binding to dyed hair are done using the hair bundles described in Examples 1, 2, or 3. The hair samples are assembled in bundles consisting of 100 hairs about 1 cm long which are bundled together using narrow tape at one end. The hair bundles are incubated in SUPERBLOCK® blocking buffer (Pierce Chemical) for 1 hour at room temperature (~22° C.), followed by 3 washes with TBST (TBS in 0.05% TWEEN®

20). Peptide binding buffer consisting of various concentrations of biotinylated peptide in TBST and 10 mg/mL BSA is added to the hair bundles and is then incubated for 1 hour at room temperature, followed by 6 TBST washes. Then, the streptavidin-horseradish peroxidase (HRP) conjugate (Pierce Chemical Co., Rockford, Ill.) is added to each well (1.0 µg per well), and then is incubated for 1 h at room temperature, followed by 6 times of washes with TBST. All hair bundles are transferred to new tubes and then the color development and the absorbance measurements are performed following the standard protocols. The results are plotted as $A_{450}$ versus the concentration of peptide using GraphPad Prism 4.0 (GraphPad Software, Inc., San Diego, Calif.). The $MB_{50}$ values are calculated from Scatchard plots and are shown Example 5 (Prophetic)

Preparation of a Peptide-Based-Carbon Black Hair Colorant

The purpose of this Example is to prepare a peptide-based-carbon black hair colorant by covalently linking a hair-binding peptide to the surface of carbon black particles. The surface of the carbon black particles are functionalized by reaction with 2,2'-azobis(2-methylpropionamide)-dihydrochloride to introduce free amino groups. The functionalized carbon black particles are then covalently linked to the specific hair-binding peptide.

Functionalization of Carbon Black Surface:

Carbon black (Nipex 160-IQ from Degussa, Allendale, N.J.), 2.0 g, and 1.0 g of 2,2'-Azobis(2-methylpropionamide) dihydrochloride (Aldrich, Milwaukee, Wis.) is added to a 100 mL round-bottom flask and 30 mL of dioxane is added. The flask is purged with nitrogen for 5 min. Then, the flask is sealed with a rubber septum and the reaction mixture is stirred at 65° C. for 14 h. After this time, 50 mL of deionized water is added to the mixture. The diluted solution is centrifuged to collect the functionalized carbon black particles and to remove the organic solvent and unreacted reagents. The carbon black particles are washed with deionized water and centrifuged. This washing and centrifuging process is repeated 2 more times. The functionalized carbon black particles are then dried by lyophilization.

Synthesis of t-Boc-Protected Hair-Binding Peptide

The purpose of this reaction is to protect the amino end group of the hair-binding peptide. One of the present hair-binding peptides (0.1 mmoles) is mixed with 2.5 mL of deionized water in a 25 mL round-bottom flask. Then, 20 mg of NaOH and 0.25 mL of t-butyl alcohol are added. After stirring the mixture for 2 min, 0.12 g of di-tert-butyl dicarbonate (t-Boc anhydride) (Aldrich) is added dropwise. The flask is sealed with a rubber septum and the reaction mixture is stirred overnight at room temperature. Upon addition of water (10 mL), the reaction mixture forms a milky emulsion, which is then extracted three times with 5 mL portions of methylene chloride. The organic layer is washed twice with 5 mL portions of deionized water. The clear water layers are all combined and dried by lyophilization, yielding 0.20 g of a fluffy white powder (80% yield). The product is analyzed by liquid chromatography-mass spectrometry (LC-MS) to determine molecular weight and purity.

Coupling of Amino-Functionalized Carbon Black with t-Boc-Peptide:

Amino-functionalized carbon black (87 mg), t-Boc-D21-peptide (80 mg) and dicyclohexyl carbodiimide (22 mg) are added to 3 mL of tetrahydrofuran (THF). A solution of dimethyl aminopyridine (17 µL) in several drops of THF is added dropwise to this mixture with stirring. The resulting suspension is heated to 40° C. for 6 h with stirring, followed by stirring overnight at room temperature. Trifluoroacetic acid (0.6 mL) is added to the product and the mixture is stirred for another 6 h. Then, 5 mL of deionized water is added to the reaction mixture. The mixture is centrifuged at 3,500 rpm for 2 min and the supernatant is decanted. The solid remaining in the centrifuge tube is washed with deionized water and centrifuged again. This washing is repeated until the pH of supernatant reaches approximately 6.0. The residue is then dried using a lyophilizer for 2 days.

Example 6

Prophetic

Hair Dyeing Using a Peptide-Based-Carbon Black Hair Colorant

The purpose of this Example is to describe how to dye a sample of natural white hair using the peptide-based-carbon black hair colorant prepared as described in Example 5.

A bundle of natural white hair (approximately 100 pieces) (from International Hair Importers and Products Inc., Bellerose, N.Y.) is cleaned by mixing with 10 mL of 50% isopropanol for 30 min and then is washed at least 5 times with distilled water. After drying in air, the cleaned hair is immersed for 30 min in a solution containing 50 mg of the hair-binding peptide-carbon black hair colorant (as described in Example 4) is dissolved in 10 mL of distilled water. After dying, the hair is washed at least 5 times with distilled water. The hair is washed three times with a 30% shampoo solution (Pantene Pro-V shampoo) by immersing the hair in the shampoo solution and stirring with a glass pipette. The hair is then rinsed at least 10 times with distilled water.

Example 7

Prophetic

Coloring Hair Using a Conjugate Comprising a Dyed-Hair-Binding Peptide Coupled to a Hair Conditioner as Sealant The purpose of this Example is to describe how to prepare a peptide-based conditioner using one of the present dyed-hair-binding peptides covalently bound to a hair conditioner as a sealant. This example is based on the method described in co-pending U.S. patent application Ser. No. 11/512,910 (corresponding to U.S. Patent Application Publication No. 2007/0067924).

Preparation of Octadecyl-Dyed-Hair-Binding Peptide Conjugate:

Octadecylisocyanate (70 mg, Aldrich, CAS No. 112-96-9) is dissolved in 5 mL of N,N'-dimethylformamide (DMF) and is then added to a solution of unprotected dyed-hair-binding peptide having a cysteine residue added to the C-terminus (150 mg), which is then dissolved in 10 mL of DMF. Triethylamine (30 mg) is then added to catalyze the reaction. The solution is stirred at room temperature (~22° C.) for approximately 120 hours. The solvent is then evaporated and the resulting solid (typically a powder) is recovered. The solid product is analyzed by gas chromatography-MALDI mass spectrometry to confirm that the octadecyl units are covalently attached to the peptide.

Hair Coloring:

The octadecyl-dyed-hair-binding peptide conjugate (29 mg) is added to 10 g of a 0.5 wt % stock solution of Basic Violet #2 (Aldrich, Milwaukee, Wis.; CAS 3248-91-7) in water and the solution is stirred overnight. A natural white hair swatch (International Hair Importers & Products Inc., Bellerose, N.Y.) is inserted into a 13 mm×100 mm test tube and 8 mL of the conjugate/dye mixture is injected into the test tube. The hair swatch is stirred in contact with the colorant solution for 30 min using a magnetic stirrer; then is removed and air dried for 30 min (simultaneous dyeing and sealing).

The dyed hair swatch is then subjected to a water rinse using copious amounts of deionized water, followed by eight shampoo treatments over a period of several days. The shampoo treatment involves the application of a commercially available shampoo, Pantene Pro-V Sheer Volume (Proctor & Gamble, Cincinnati, Ohio), to the dyed hair as follows. A quarter-sized drop of the shampoo is distributed evenly over the dyed hair swatch and then is massaged aggressively into the dyed hair for 30 sec, after which the dyed hair swatch is rinsed with water to remove the shampoo. The dyed hair swatch is then dried at room temperature.

The procedure described above is repeated without the addition of the conjugate sealant to serve as a control. Color durability is rated qualitatively using visual observation of color retention against the control.

After the shampoo treatment, the color of the dyed hair swatch treated with the dye and the octadecyl-dyed-hair-binding peptide sealant is evaluated for improvement in color retention compared to the control (see Example 3).

Example 8

Prophetic

Preparation of a Peptide-Based Hair Conditioner

The purpose of this Example is to describe how to prepare a peptide-based hair conditioner by covalently linking one of the present dyed-hair-binding peptides (functionalized with a cysteine residue) with octylamine using the heterobifunctional cross-linking agent 3-maleimidopropionic acid N-hydroxysuccinimide ester.

Octylamine, obtained from Aldrich (Milwaukee, Wis.) is diluted by adding 11.6 mg to 0.3 mL of DMF. This diluted solution is added to a stirred solution containing 25 mg of 3-maleimidopropionic acid N-hydroxysuccinimide ester (Aldrich) and 5 mg of diisopropylethylamine (Aldrich) in 0.2 mL of DMF in a 5 mL round bottom flask. The solution is stirred for 4 h. The solution is then dried under high vacuum. The product, octylamine-attached maleimidopropionate, is purified by column chromatography using a Silica gel 60 (EMD Chemicals, formerly EM Science, Gibbstown, N.J.) column and DMF/ether as the eluent.

Approximately 12 mg of the above product is placed into a 5 mL round bottom flask and 50 mg of a cysteine-functionalized dyed-hair-binding peptide (the cysteine functionalized version of one of the present dyed-hair-binding peptides can be obtained from SynPep, Dublin, Calif.) and 0.5 mL of 0.1 M phosphate buffer at pH 7.2 are added. This mixture is stirred at room temperature for 6 h. The final product, the peptide-based hair conditioner, is purified by extraction with water/ether.

Example 9

Prophetic

Preparation of a Peptide-Polysiloxane Hair Conditioner

The purpose of this Example is to describe how to synthesize a peptide-polysiloxane hair conditioner. The reactive side functional groups of the peptide are fully protected so that the reaction with the polysiloxane proceeds only with the C-terminal group of the peptide. In addition, a tripeptide spacer, consisting of glycine residues, is added to the C-terminal end of the binding sequence.

Fifty milligrams of the fully protected dyed-hair-binding peptide is dissolved in 1 mL of dimethylformamide (DMF, from E. Merck, Darmstadt, Germany) in a 5 mL round bottom flask. Polysiloxane fluid 2-8566 (77 mg) (N %=0.875%, 0.024 mmol of —$NH_2$, from Dow Corning, Midland, Mich.) is dissolved in 2 mL of THF (E. Merck) in a sample vial, then is transferred into the round bottom flask containing the peptide solution. Then, 5 mg of dicyclohexyl carbodiimide (DCC, 0.024 mmol) and 5 µL of dimethylaminopyridine (DMAP) is added to the flask. The flask is sealed with a rubber stopper and the reaction mixture is stirred at 50° C. for 5 h and then, at room temperature overnight. After the reaction is completed, the solvent is pumped out under vacuum until a solid product is formed.

The solid product is dissolved in N,N-dimethylacetamide (DMAC, from EMD Chemicals) and 5 mg/mL of the product solution in DMAC is prepared for GPC (gel permeation chromatography) analysis with refractive index detection to determine the molecular weight.

A cleavage reagent (referred to as Reagent K) having the following composition:
trifluoroacetic acid/H2O/thioanisole/ethanedithiol/phenol (85:5:5:2.5:2.5, by volume) is used to cleave the protecting groups from the side functional groups of the peptide. Reagent K (1 mL) is pre-cooled to −20° C. and then, is added to 100 mg of the peptide-polysiloxane conditioner. The mixture is stirred for 3-4 h at room temperature and then Reagent K is removed under high vacuum. Then, the Fmoc protecting group is removed from the N-terminus of the peptide by adding 61.2 mg of 20 vol % piperidine in DMF to the mixture and stirring for 30 min, followed by pumping under high vacuum.

Example 10

Prophetic

Preparation of a Peptide-Based Hair Colorant

The purpose of this Example is to describe how to prepare a peptide-based hair colorant by covalently attaching one of the present dyed-hair-binding peptides to Disperse Orange 3 dye. The dye is first functionalized with isocyanate and then reacted with the peptide.

Functionalization of Disperse Orange 3:

In a dry box, 14.25 g of Disperse Orange 3 (Aldrich) is suspended in 400 mL of dry THF in an addition funnel. A 2-liter, four-neck reaction flask (Corning Inc., Corning, N.Y.; part no. 1533-12), containing a magnetic stir bar, is charged with 200 mL of dry toluene. The flask is fitted with a cold finger condenser (Corning Inc., part no. 1209-04) and with a second cold finger condenser with an addition funnel, and is placed on an oil bath in a hood.

Phosgene (25.4 mL) is condensed into the reaction flask at room temperature. After phosgene addition is complete, the temperature of the oil bath is raised to 80° C. and the Disperse Orange 3 suspension is added to the reaction flask dropwise in 100 mL increments over 2 h, while monitoring the reaction temperature and gas discharge from the scrubber. The temperature is maintained at or below 64° C. throughout the addition. After addition is complete, the reactants are heated at 64° C. for 1 h and then allowed to cool to room temperature with stirring overnight.

The reaction solvents are vacuum-distilled to dryness, while maintaining the contents at or below 40° C., and vacuum is maintained for an additional hour. The reaction flask is transferred to a dry box; the product is collected and is dried overnight (15.65 g). The desired product can be confirmed by proton NMR.

Coupling of Isocyanate Functionalized Dye with a Hair-Binding Peptide:

Isocyanate functionalized Disperse Orange 3 [(2-(4-isocyanatophenyl)-1-(4-nitrophenyl)diazene] (16 mg), prepared as described above, is dissolved in 5 mL of DMF and is added to a solution containing 75 mg of non-protected dyed-hair-binding peptide dissolved in 10 mL of DMF. The solution is stirred at room temperature for 24 h. The solvent is evaporated and the solid is collected. The product can then be analyzed by MALDI mass spectrometry to confirm covalent attachment of the dye molecule to the dyed-hair-binding peptide.

What is claimed is:

1. A dyed-hair-binding peptide comprising a sequence selected from the group consisting of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, and 34.

2. A peptide-based hair reagent having the general structure (DHBP)$_n$—BA or [(DHBP)$_m$—S]$_n$-BA; wherein
a) DHBP is a dyed-hair-binding peptide according to claim 1;
b) BA is a benefit agent;
c) n ranges from 1 to about 1,000;
d) m ranges from 1 to about 50; and
e) S is a spacer.

3. The peptide-based hair reagent according to claim 2 wherein the benefit agent is selected from the group consisting of conditioners, colorants, and sunscreen agents.

4. The peptide-based hair reagent according to claim 3 wherein the conditioner is selected from the group consisting of cationic polymers, cationic surfactants, fatty alcohols, fatty amines, waxes, esters, nonionic polymers, silicones, siloxanes, polymer emulsions, nanoparticles, and mixtures thereof.

5. The peptide-based hair reagent according to claim 3 wherein the colorant is selected from the group consisting of dyes, pigments, and colored microspheres.

6. The peptide-based hair reagent according to claim 5 wherein the dye is selected from the group consisting of 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, Henna, HC Blue 1, HC Blue 2, HC Yellow 4, HC Red 3, HC Red 5, Disperse Violet 4, Disperse Black 9, HC Blue 7, HC Blue 12, HC Yellow 2, HC Yellow 6, HC Yellow 8, HC Yellow 12, HC Brown 2, D&C Yellow 1, D&C Yellow 3, D&C Blue 1, Disperse Blue 3, Disperse violet 1, eosin derivatives, and halogenated fluorescein derivatives.

7. The peptide-based hair reagent according to claim 5 wherein the pigment is selected from the group consisting of D&C Red No. 36, D&C Orange No. 17, the calcium lakes of D&C Red Nos. 7, 11, 31 and 34, the barium lake of D&C Red No. 12, the strontium lake of D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, titanium dioxide, titanium dioxide nanoparticles, zinc oxide, barium oxide, ultramarine blue, bismuth citrate, and carbon black particles.

8. The peptide-based hair reagent according to claim 5 wherein the colored microsphere is comprised of materials selected from the group consisting of polystyrene, polymethylmethacrylate, polyvinyltoluene, styrene/butadiene copolymer, and latex.

9. The peptide-based hair reagent according to claim 2 wherein the spacer is selected from the group consisting of ethanol amine, ethylene glycol, polyethylene with a chain length of 6 carbon atoms, polyethylene glycol with 3 to 6 repeating units, phenoxyethanol, propanolamide, butylene glycol, butyleneglycolamide, propyl phenyl chains, ethyl alkyl chains, propyl alkyl chains, hexyl alkyl chains, steryl alkyl chains, cetyl alkyl chains, and palmitoyl alkyl chains.

10. The peptide-based hair reagent according to claim 2 wherein the spacer is a peptide having a length of about 1 to about 50 amino acids.

11. The peptide-based hair reagent of claim 2 wherein the spacer is a peptide comprising amino acids selected from the group consisting of glycine, alanine, serine, proline, and mixtures thereof.

12. A hair care composition comprising an effective amount of the peptide-based hair reagent according to claim 2 or an effective amount of at least one of the dyed-hair-binding peptide according to claim 1.

13. A method for applying a benefit agent to dyed hair comprising contacting hair with the peptide-based hair reagent according to claim 2 under conditions whereby the dyed-hair-binding peptide adheres to dyed hair.

14. The method according to claim 13 wherein the peptide-based hair reagent has a binding affinity for hair of MB$_{50}$ of $10^{-6}$ M or less.

15. A method to form a protective layer on the surface of dyed hair comprising contacting dyed hair with a hair care composition comprising an effective amount of the peptide-based hair reagent according to claim 2 or an effective amount of at least one of the dyed-hair-binding peptide according to claim 1, whereby the dyed-hair-binding peptide adheres to said dyed hair.

16. The method according to either claim 13 or 15 wherein the dyed hair is dyed using a dye selected from the group consisting of 4-hydroxypropylamino-3-nitrophenol, 4-amino-3-nitrophenol, 2-amino-6-chloro-4-nitrophenol, 2-nitro-paraphenylenediamine, N,N-hydroxyethyl-2-nitro-phenylenediamine, 4-nitro-indole, 2-nitro-5-glyceryl methylaniline, 3-metylamino-4-nitrophenoxyethanol, 3-nitro-p-hydroxyethylaminophenol, hydroxyanthraquinoneaminopropylmethyl morpholinium methosulfate, Henna, HC Blue 1, HC Blue 2, HC Yellow 4, HC Red 3, HC Red 5, HC Red 7, HC Violet 1, HC Violet 2, HC Blue 7, HC Blue 10, HC Blue 12, HC Yellow 2, HC Yellow 6, HC Yellow 8, HC Yellow 12, HC Orange 2, HC Orange 3, HC Brown 2, D&C Yellow 1, D&C Yellow 3, D&C Blue 1, Disperse Blue 3, Disperse Violet 1, Disperse Orange, Disperse Violet 4, Disperse Black 9, Basic Orange 31, Basic Yellow 57, Basic Yellow 87, HC Yellow No. 9, Basic Blue 26, Basic Blue 7, Basic Blue 99, Basic Violet 14, Basic Violet 2, Basic Brown 16, Basic Brown 17, Basic Red 2, Basic Red 51, Basic Red 76, Acid Red 33, Acid Violet 43, Brilliant Black 1, eosin derivatives, halogenated fluorescein derivatives and dihydroxyacetone.

* * * * *

SEQUENCE LISTING

```
<160> NUMBER OF SEQ ID NOS: 38

<210> SEQ ID NO 1
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 1

Ser Ser Asn Tyr Asn Tyr Asn Tyr Asn Tyr Gln Tyr Ser Ser Arg
1               5                   10                  15

<210> SEQ ID NO 2
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 2

Ser Ser Leu Leu Ser Asp Phe His Tyr Gly Asp Met Trp Asp Ala Ser
1               5                   10                  15

Arg

<210> SEQ ID NO 3
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 3

Ser Ser Ser Ser Asn Asp Ser Asn Val Ser Trp Phe His Tyr Tyr Ala
1               5                   10                  15

Ser Gly Leu Thr Ser Ser Arg
            20

<210> SEQ ID NO 4
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 4

Ser Ser Ser Ser Leu Asp Phe Phe Ser Tyr Ser Ala Phe Ser Gly Gly
1               5                   10                  15

Val Ala Glu Ser Arg
```

<210> SEQ ID NO 5
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 5

Ser Ser Ser Ser Ala Asp Ala Ala Tyr Gly His Cys Cys Gly Ala Gly
1               5                   10                  15

Phe Ser Thr Phe Ser Ser Arg
            20

<210> SEQ ID NO 6
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 6

Ser Ser Ser Ser Asp Val His Asn Ser Ile Ile Gly Trp Asp Phe Tyr
1               5                   10                  15

His Ser Arg Gly Ser Ser Arg
            20

<210> SEQ ID NO 7
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 7

Ser Ser Ser Cys Tyr Asp Val Glu Cys Ser Ser Phe Val Ala Trp Met
1               5                   10                  15

Arg Gly Pro Ser Ser Arg
            20

<210> SEQ ID NO 8
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 8

Ser Ser Tyr Tyr Asn Tyr His Tyr Gln Tyr Gln Asp Ser Ser Arg
1               5                   10                  15

<210> SEQ ID NO 9
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 9

Ser Ser Leu Phe Asn Met Tyr Gly His Gln Ser Val Leu Gly Pro Ser
1               5                   10                  15

Arg

<210> SEQ ID NO 10

```
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 10

Ser Ser Phe Ser Val Asn Glu Pro His Ala Trp Met Ala Pro Leu Ser
1               5                   10                  15

Arg

<210> SEQ ID NO 11
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 11

Ser Ser Phe Ser Trp Val Tyr Gly His Gly Gly Leu Gly Phe Ala Ser
1               5                   10                  15

Arg

<210> SEQ ID NO 12
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 12

Ser Ser Phe Val Ser Trp Ser Pro Tyr Lys Ser Pro Pro Glu Leu Ser
1               5                   10                  15

Arg

<210> SEQ ID NO 13
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 13

Ser Ser Gly Ser Val Ala Val Ser Ala Glu Ala Ser Trp Phe Ser Gly
1               5                   10                  15

Val Ala Ala Ser Arg
            20

<210> SEQ ID NO 14
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 14

Ser Ser Phe Tyr Gly Ser Ser Ala Phe Val Ser Ser Gly Val Ser Val
1               5                   10                  15

Ala Tyr Gly Ser Arg
            20

<210> SEQ ID NO 15
<211> LENGTH: 15
<212> TYPE: PRT
<213> ORGANISM: artificial sequence
```

```
<220> FEATURE:
<223> OTHER INFORMATION: Dyed-hair-bindg peptide

<400> SEQUENCE: 15

Ser Ser His Tyr Tyr Tyr Asn Asp Tyr Asp His Gln Ser Ser Arg
1               5                   10                  15

<210> SEQ ID NO 16
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 16

Ser Ser Leu Phe Ser Asp Val His Tyr Gly Ser Asn Lys Ala Leu Ser
1               5                   10                  15

Arg

<210> SEQ ID NO 17
<211> LENGTH: 17
<212> TYPE: PRT
<213> ORGANISM: artificial sequence
<220> FEATURE:
<223> OTHER INFORMATION: Dyed-hair-bindg peptide

<400> SEQUENCE: 17

Ser Ser Ser Phe Ala Tyr Leu Val Pro Asp Asp Gly Trp Leu Ser Ser
1               5                   10                  15

Arg

<210> SEQ ID NO 18
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 18

Ser Ser Ser Cys Met Gly Ser His Asn Pro Arg Met Ser Val Glu Glu
1               5                   10                  15

Ser Thr Arg Asn Cys Ser Arg
            20

<210> SEQ ID NO 19
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 19

Ser Ser Ser Cys Asn Asn Asn Trp Phe Tyr Ser Ser Thr Leu Pro Gly
1               5                   10                  15

Gly Asp His Ala Cys Ser Arg
            20

<210> SEQ ID NO 20
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 20
```

```
Ser Ser Ser Gly Ala Val Phe Ser Ser Gly Gly Ala Asp Ala Gly Trp
1               5                   10                  15

Gly Val Trp Ser Arg
            20

<210> SEQ ID NO 21
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 21

Ser Ser Ser Phe Ala Ala Ser Ser Ala Phe Ser Phe Leu Val Asp Ala
1               5                   10                  15

Val Ala Trp Ser Arg
            20

<210> SEQ ID NO 22
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 22

Ser Ser Val Asp Tyr Glu Val Pro Leu Ala Val Ala Ala Glu Trp Gly
1               5                   10                  15

Phe Ser Val Ser Arg
            20

<210> SEQ ID NO 23
<211> LENGTH: 21
<212> TYPE: PRT
<213> ORGANISM: artificial sequence
<220> FEATURE:
<223> OTHER INFORMATION: Dyed-hair-bindg peptide

<400> SEQUENCE: 23

Ser Ser Ala Asp Phe Ala Ser Phe Gly Phe Gly Phe Ser Ala Ala
1               5                   10                  15

Ser Ala Asp Ser Arg
            20

<210> SEQ ID NO 24
<211> LENGTH: 23
<212> TYPE: PRT
<213> ORGANISM: artificial sequence
<220> FEATURE:
<223> OTHER INFORMATION: Dyed-hair-bindg peptide

<400> SEQUENCE: 24

Ser Ser Phe Ala Glu Ala Trp Ser Arg Ala Trp Pro Arg Ala Glu Val
1               5                   10                  15

Phe Phe Pro Ser Arg Gly Tyr
            20

<210> SEQ ID NO 25
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 25
```

-continued

Ser Ser His Asp Glu His Tyr Gln Tyr His Tyr Tyr Ser Ser Arg
1               5                   10                  15

<210> SEQ ID NO 26
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 26

Ser Ser Tyr Tyr Tyr Asp Tyr Tyr Gln Gln Asp Tyr Ser Ser Arg
1               5                   10                  15

<210> SEQ ID NO 27
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 27

Ser Ser Gln Tyr Tyr Gln Asp Tyr Gln Tyr Tyr His Ser Ser Arg
1               5                   10                  15

<210> SEQ ID NO 28
<211> LENGTH: 15
<212> TYPE: PRT
<213> ORGANISM: artificial sequence
<220> FEATURE:
<223> OTHER INFORMATION: Dyed-hair-bindg peptide

<400> SEQUENCE: 28

Ser Ser Tyr His Tyr Asp Tyr Asp His Tyr Tyr Glu Ser Ser Arg
1               5                   10                  15

<210> SEQ ID NO 29
<211> LENGTH: 18
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (18)..(18)
<223> OTHER INFORMATION: Site of biotin attachment

<400> SEQUENCE: 29

Asn Tyr Asn Tyr Asn Tyr Asn Tyr Gln Tyr Ser Ser Arg Gly Ser Ser
1               5                   10                  15

Gly Lys

<210> SEQ ID NO 30
<211> LENGTH: 26
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (26)..(26)
<223> OTHER INFORMATION: Site of biotin attachment

<400> SEQUENCE: 30

Ser Ser Asn Asp Ser Asn Val Ser Trp Phe His Tyr Tyr Ala Ser Gly
1               5                   10                  15

Leu Thr Ser Ser Arg Gly Ser Ser Gly Lys
            20                  25

```
<210> SEQ ID NO 31
<211> LENGTH: 20
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (20)..(20)
<223> OTHER INFORMATION: Site of biotin attachment

<400> SEQUENCE: 31

Leu Leu Ser Asp Phe His Tyr Gly Asp Met Trp Asp Ala Ser Arg Gly
 1               5                  10                  15

Ser Ser Gly Lys
            20

<210> SEQ ID NO 32
<211> LENGTH: 18
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (18)..(18)
<223> OTHER INFORMATION: Site of biotin attachment

<400> SEQUENCE: 32

Tyr Tyr Tyr Asp Tyr Tyr Gln Gln Asp Tyr Ser Ser Arg Gly Ser Ser
 1               5                  10                  15

Gly Lys

<210> SEQ ID NO 33
<211> LENGTH: 17
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (17)..(17)
<223> OTHER INFORMATION: Site of biotin attachment

<400> SEQUENCE: 33

Gln Tyr Tyr Gln Asp Tyr Gln Tyr His Ser Ser Arg Gly Ser Ser
 1               5                  10                  15

Lys

<210> SEQ ID NO 34
<211> LENGTH: 18
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (18)..(18)
<223> OTHER INFORMATION: Site of biotin attachment

<400> SEQUENCE: 34

Tyr His Tyr Asp Tyr Asp His Tyr Tyr Glu Ser Ser Arg Gly Ser Ser
 1               5                  10                  15

Gly Lys

<210> SEQ ID NO 35
```

```
<211> LENGTH: 46
<212> TYPE: PRT
<213> ORGANISM: artificial sequence
<220> FEATURE:
<223> OTHER INFORMATION: Dyed-hair-bindg peptide

<400> SEQUENCE: 35

Ser Ser Asn Asp Ser Asn Val Ser Trp Phe His Tyr Tyr Ala Ser Gly
1               5                   10                  15

Leu Thr Ser Ser Arg Gly Ser Ser Gly Ser Arg Lys Ser Ser Gln Lys
            20                  25                  30

Asn Pro His His Pro Lys Pro Pro Lys Lys Pro Thr Ala Arg
        35                  40                  45

<210> SEQ ID NO 36
<211> LENGTH: 51
<212> TYPE: PRT
<213> ORGANISM: artificial sequence
<220> FEATURE:
<223> OTHER INFORMATION: Dyed-hair-bindg peptide
<220> FEATURE:
<221> NAME/KEY: MISC_FEATURE
<222> LOCATION: (51)..(51)
<223> OTHER INFORMATION: Site of biotin attachment

<400> SEQUENCE: 36

Ser Ser Asn Asp Ser Asn Val Ser Trp Phe His Tyr Tyr Ala Ser Gly
1               5                   10                  15

Leu Thr Ser Ser Arg Gly Ser Ser Gly Ser Arg Lys Ser Ser Gln Lys
            20                  25                  30

Asn Pro His His Pro Lys Pro Pro Lys Lys Pro Thr Ala Arg Gly Ser
        35                  40                  45

Ser Gly Lys
    50

<210> SEQ ID NO 37
<211> LENGTH: 5
<212> TYPE: PRT
<213> ORGANISM: artificial sequence
<220> FEATURE:
<223> OTHER INFORMATION: Synthetic peptide tag for attaching biotin

<400> SEQUENCE: 37

Gly Ser Ser Gly Lys
1               5

<210> SEQ ID NO 38
<211> LENGTH: 5
<212> TYPE: PRT
<213> ORGANISM: artificial sequence
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any naturally occurring amino acid
      except Pro, Glu, Asp, Gln, Lys, and Arg.

<400> SEQUENCE: 38

Asp Met Gln Asp Xaa
1               5
```